US007427485B2

(12) United States Patent
Greengard et al.

(10) Patent No.: US 7,427,485 B2
(45) Date of Patent: Sep. 23, 2008

(54) METHOD FOR CLASSIFICATION OF ANTI-PSYCHOTIC DRUGS

(75) Inventors: Paul Greengard, New York, NY (US); Gilberto Fisone, Stockholm (SE)

(73) Assignee: The Rockefeller University, New York, NY (US)

( * ) Notice: Subject to any disclaimer, the term of this patent is extended or adjusted under 35 U.S.C. 154(b) by 424 days.

(21) Appl. No.: 10/233,448

(22) Filed: Sep. 3, 2002

(65) Prior Publication Data

US 2003/0109419 A1 Jun. 12, 2003

Related U.S. Application Data

(60) Provisional application No. 60/316,338, filed on Aug. 31, 2001.

(51) Int. Cl.
*C12Q 1/48* (2006.01)
*C12Q 1/42* (2006.01)
*G01N 33/53* (2006.01)

(52) U.S. Cl. .............................. 435/7.1; 435/15; 435/21
(58) Field of Classification Search ................... 435/15, 435/19, 7.1, 7.2, 7.21; 424/9.2
See application file for complete search history.

(56) References Cited

U.S. PATENT DOCUMENTS

2003/0171255 A1 9/2003 Greengard et al.

FOREIGN PATENT DOCUMENTS

| EP | 02757518.2 | 6/2006 |
|---|---|---|
| WO | WO 99/20273 | 4/1999 |
| WO | WO 03/014321 | 2/2003 |

OTHER PUBLICATIONS

G. E. Duncan et al. " Comparison of the Effects of Clozapine, Risperidone, and Olanzapine on Ketamine-Induced Alterations in Regional Brain Metabolism", J. Pharmacol. Exp. Therapeutics. 293(1): 8-14. (2000).*
S.A. Varvel et al. "Effects of Antipsychotic Drugs on Operant Responding After Acute and Repeated Administration", Psychophamacology 160: 182-191. (2002).*
B. Yang et al. "Phosphorylation of ERK and CREB In Cultured Hippocampal Neurons After Haloperidol and Risperidone Administration", Psychiatry Clin. Neurosci. 58: 262-267. (2004).*
X. Lu et al. "Olanzapine Produces Trophic Effects In Vitro and Stimulates Phosphorylation of Akt/PKB, ERK1/2, and the Mitogen-Activated Protein Kinase p38", Brain Research 1011: 58-68. (2204).*
J.L. Browning et al. "Clozapine and the Mitogen-Activiated Protein Kinase Signal Transduction Pathway: Implications For Antipsychotic Actions", Biological Psychiatry 57(6):617-623. (2005).*
Boutlon et al., "ERKs: A Family of Protein-Serine.Threonine Kinases That Are Activated and Tyrosine Phosphorylated in Response to Insulin", Cell (1991) 65:663-675.

Braff et al., "Gating and Habituation of the Startle Reflex in Schizophrenic Patients", Arch Gen Psychiatry (1992) 49:206-215.
Cesare et al., "Transcriptional Regulation by Cyclic AMP-Responsive Factors", Progress In Nucleic Acids Research (2000) 64:343-369.
Fujimura et al., "The effect of the antipsychotic drug mosapramine on the expression of Fos protein in the rat brain Comparison with haloperidol, clozapine, and risperidone", Life Sciences (2000) 67:2865-2872.
Ghosh et al., "Calcium Regulation of Gene Expression in Neuronal Cells", Journal of Neurobiology (1994) 25:294-303.
Greengard et al., "Beyond the Dopamine Receptor: the DARPP-32 Protein Phosphatase-1 Cascade", Neuron (1999) 23:435-447.
Guitart et al., "Chronic Administration of Lithium or Other Antidepressants Increases Levels of DARPP-32 in Rat Frontal Cortex", Journal of Neurochemistry (1992) 59:1164-1167.
Huang et al., "The Matter of Mind: Molecular Control of Memory", Essays Biochem (1998) 33:165-78.
Lamprecht R., "CREB: a message to remember", Cell Mol. Life Sci. (1999) 55:554-563.
Millan et al., "S18327 (1-(2-[4-(6-Fluoro-1, 2-benzisoxazol-3-yl)piperid-1-yl]ethyl)3-phenyl imidazolin-2-one), a Novel, Potential Antipsychotic Displaying Marked Antagonist Properties at $\alpha_1$- and $\alpha_2$ -Adrenergic Receptors: II Functional Profile and a Multiparametric Comparison with Heloperidol, Clozapine, and 11 other Antipsychotic Agents", The Journal of Pharmacology and Experimental Therapeutics (2000) 292: 54-66.
Robertson et al., "Induction Patterns of Fos-Like Immunoreactivity in the Forebrain as predictors of Atypical Antipsychotic Activity", The Journal of Pharmacology and Experimental Therapeutics (1994) 271:1058-1066.
Silverstone, T., "Clinically relevant differences between antipsychotic compounds", Acta Psychiatr Scand (1990) 82:88-91.
Stroppolo et al., "Role of phosphatidylinositide 3-kinase in brain derived neurotrophic factor-induced DARPP-32 expression in medium size spiny neurons *in vitro*", Journal of Neurochemistry (2001) 79:1027-1032.
Sweatt, J.D., "The neuronal MAP kinase cascade: a biochemical signal integration system subserving synaptic plasticity and memory", Journal of Neurochemistry (2001) 76:1-10.
Swerdlow et al., "Clozapine and Haloperidol in an Animal Model of Sensorimotor Gating Deficits in Schizophrenia", Pharmacology Biochemistry and Behavior (1993) 44:741-744.

(Continued)

*Primary Examiner*—Rebecca Prouty
(74) *Attorney, Agent, or Firm*—Hoxie & Associates LLC; Thomas Hoxie; Brittany La

(57) ABSTRACT

The present invention provides a method for identifying an agent to be tested for an ability to treat a psychotic disorder in a patient in need of such treatment. The invention provides a method for screening candidate drugs for anti-psychotic drug activity, preferably atypical anti-psychotic activity, comprising contacting cells or tissues with a candidate drug, determining levels of phosphorylation of the intracellular signaling proteins, DARPP-32, ERK1, ERK2 and CREB, in said cells or tissues and determining the pattern of the levels of phosphorylation of the proteins. The pattern of the levels of phosphorylation of DARPP-32, ERK1, ERK2 and CREB is, in certain embodiments, compared with the pattern of the levels of phosphorylation of DARPP-32, ERK1, ERK2 and CREB in the presence of an atypical anti-psychotic drug.

17 Claims, No Drawings

OTHER PUBLICATIONS

Walaas et al., "A dopamine-and cyclic AMP-regulated phosphoprotein enriched in dopamine-innervated brain regions", Nature (1983) 301:69-71.

Wettstein et al., "Selectivity of Action of Typical and Atypical Anti-Psychotic Drugs as Antagonists of the Behavioral Effects of 1-[2,5-Dimethoxy-4-lodophenyl]-2-Aminopropane (DOI)", Prog Neuro-Psychopharmacol & Biol Psychiat (1999) 23:533-544.

Bibb, J. A. et al. "Phosphorylation of DARPP-32 by Cdk5 Modulates Dopamine Signalling in Neurons", Nature, Dec. 2, 1999, vol. 402, pp. 669-671, see entire article.

Nishi, A. et al. "Amplification of Dopaminergic Signaling by a Positive Feedback Loop", PNAS. Nov. 7, 2000. vol. 97, No. 23, pp. 12840-12845, see particurlarly Fig. 6.

PCT International Search Report for PCT/US02/27802 filed Sep. 3, 2002.

Alessandrini et al., 1992 "Phorbol Ester Stimulates a Protein-Tyroisine/Threonine Kinase That Phosphorylates and Activates the Erk-1 Gene Product," Proc Natl. Acad Sci. USA, 89: 8200-8204.

Robbins et al., 1993, "Regulation and Properties of Extracellular Signal-Regulated Protein Kinases 1 and 2 in Vitro," J. Biol. Chem., 268(7):5097-5106.

Cole et al., "Neuronal Adaptation to Amphetamine and Dopamine: Molecular Mechanisms of Prodynorphin Gene Regulation in Rat Striatum," Neuron, 14(4):813-823 (Apr. 1995).

Kyosseva et al., "Differential and Region-Specific Activation of Mitogen-Activated Protein Kinases Following Chronic Administration of Phencyclidine in Rat Brain," Neuropsychopharmacology, 24(3):267-277 (Mar. 2001).

Thome et al., "Induction of CREB Phosphorylation and CRE-Mediated Gene Transcription by Antipsychotic Drugs," Society for Neuroscience Abstracts, 26(1-2): Abstract No. -149.13 (2000).

* cited by examiner

SEQUENCE LISTING

<160> NUMBER OF SEQ ID NOS: 8

<210> SEQ ID NO 1
<211> LENGTH: 204
<212> TYPE: PRT
<213> ORGANISM: Homo sapiens

<400> SEQUENCE: 1

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Asn Glu Asn Gln Ala Ser Glu Glu Asp Glu Leu Gly Glu Leu Arg
            100                 105                 110

Glu Leu Gly Tyr Pro Arg Glu Glu Asp Glu Glu Glu Glu Asp Asp
        115                 120                 125

Glu Glu Glu Glu Glu Glu Asp Ser Gln Ala Glu Val Leu Lys Val
    130                 135                 140

Ile Arg Gln Ser Ala Gly Gln Lys Thr Thr Arg Gly Leu Gly Leu Glu
145                 150                 155                 160

Gly Pro Trp Glu Arg Pro Pro Leu Asp Glu Ser Glu Arg Asp Gly
                165                 170                 175

Gly Ser Glu Asp Gln Val Glu Asp Pro Ala Leu Ser Glu Pro Gly Glu
            180                 185                 190

Glu Pro Gln Arg Pro Ser Pro Ser Glu Pro Gly Arg
        195                 200

<210> SEQ ID NO 2
<211> LENGTH: 201
<212> TYPE: PRT
<213> ORGANISM: Mus musculus

<400> SEQUENCE: 2

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Glu Glu Glu Ala Ser Pro His Gln Arg Thr Ser Gly Glu Gly
    50                  55                  60

His His Pro Lys Ser Lys Arg Pro Asn Pro Cys Ala Tyr Thr Pro Pro
65                  70                  75                  80

Ser Leu Lys Ala Val Arg Arg Leu Gln Thr Ile Ser Asn Leu Ser Glu
                85                  90                  95

Asn Gln Ala Ser Glu Glu Glu Asp Glu Leu Gly Glu Leu Arg Glu Leu
            100                 105                 110

Gly Tyr Pro Gln Glu Asp Glu Glu Asp Glu Glu Asp
         115                 120                 125

Glu Glu Glu Asp Ser Gln Ala Glu Val Leu Lys Gly Ser Arg Gly Thr
        130                 135                 140

Val Gly Gln Lys Leu Leu Val Ala Gly Val Trp Arg Gly Pro Gly Ser
145                 150                 155                 160

Ala His Leu Leu Trp Met Ser Pro Arg Glu Met Glu Thr Leu Arg Thr
                165                 170                 175

Lys Trp Lys Ala Glu Gln His Glx Val Ser Leu Glu Arg Asn Leu Ser
        180                 185                 190

Ile Pro Ala Pro Pro Glu Pro Gly Thr
        195                 200

<210> SEQ ID NO 3
<211> LENGTH: 205
<212> TYPE: PRT
<213> ORGANISM: Rattus sp.

<400> SEQUENCE: 3

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Ser Ser Pro His Gln Arg Thr Ser Gly Glu Gly His His Pro
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Thr Ile Ser Asn Leu
                85                  90                  95

Ser Glu Asn Gln Ala Ser Glu Glu Asp Glu Leu Gly Glu Leu Arg
            100                 105                 110

Glu Leu Gly Tyr Pro Asn Glu Asp Asp Glu Glu Asp Glu Asp Glu Asp
        115                 120                 125

Glu Glu Glu Asp Glu Glu Glu Asp Ser Gln Ala Glu Val Leu Lys Gly
    130                 135                 140

Ser Arg Gly Thr Ala Gly Asn Lys Leu Thr Ser Gly Gln Gly Leu Glu
145                 150                 155                 160

Gly Pro Trp Glu Arg Pro Pro Leu Asp Glu Pro Gln Arg Asp Gly
                165                 170                 175

Asn Ser Glu Asp Gln Gly Glu Gly Arg Ala Thr Gln Ser Glu Pro Gly
            180                 185                 190

Glu Glu Pro Arg His Pro Thr Pro Pro Glu Ser Gly Thr
        195                 200                 205

<210> SEQ ID NO 4
<211> LENGTH: 203
<212> TYPE: PRT
<213> ORGANISM: bovine

<400> SEQUENCE: 4

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

```
Pro Thr Pro Ala Met Leu Phe Arg Leu Ser Glu His Ser Pro Glu
            35                  40                  45

Glu Glu Ala Ser Pro His Gln Arg Ala Ser Gly Glu Gly His His Leu
 50                  55                  60

Lys Ser Lys Arg Pro Asn Pro Cys Ala Tyr Thr Pro Pro Ser Leu Lys
 65                  70                  75                  80

Ala Val Gln Arg Ile Ala Glu Ser His Leu Gln Ser Ile Ser Asn Leu
                 85                  90                  95

Gly Glu Asn Gln Ala Ser Glu Glu Asp Glu Leu Gly Glu Leu Arg
            100                 105                 110

Glu Leu Gly Tyr Pro Arg Glu Glu Glu Glu Glu Glu Glu Glu Asp
            115                 120                 125

Glu Glu Glu Glu Asp Ser Gln Ala Glu Val Leu Lys Gly Ser Arg
            130                 135                 140

Gly Ser Ala Gly Gln Lys Thr Thr Tyr Gly Gln Gly Leu Glu Gly Pro
145                 150                 155                 160

Trp Glu Arg Pro Pro Leu Asp Gly Pro Gln Arg Asp Gly Ser Ser
            165                 170                 175

Glu Asp Gln Val Glu Asp Pro Ala Leu Asn Glu Pro Gly Glu Pro
            180                 185                 190

Gln Arg Met Pro Ala His Pro Glu Pro Gly Thr
            195                 200

<210> SEQ ID NO 5
<211> LENGTH: 16
<212> TYPE: PRT
<213> ORGANISM: Homo sapiens

<400> SEQUENCE: 5

Lys Arg Pro Asn Pro Cys Ala Tyr Thr Pro Pro Ser Leu Lys Ala Val
1               5                  10                  15

<210> SEQ ID NO 6
<211> LENGTH: 341
<212> TYPE: PRT
<213> ORGANISM: Homo sapiens

<400> SEQUENCE: 6

Met Thr Met Glu Ser Gly Ala Glu Asn Gln Gln Ser Gly Asp Ala Ala
1               5                  10                  15

Val Thr Glu Ala Glu Asn Gln Gln Met Thr Val Gln Ala Gln Pro Gln
            20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
 50                  55                  60

Gln Val His Gly Val Ile Gln Ala Ala Gln Pro Ser Val Ile Gln Ser
 65                  70                  75                  80

Pro Gln Val Gln Thr Val Gln Ser Ser Cys Lys Asp Leu Lys Arg Leu
                 85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
            115                 120                 125

Ser Arg Arg Pro Ser Tyr Arg Lys Ile Leu Asn Asp Leu Ser Ser Asp
            130                 135                 140
```

```
Ala Pro Gly Val Pro Arg Ile Glu Glu Lys Ser Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
            180                 185                 190

Leu Ala Asn Asn Gly Thr Asp Gly Val Gln Gly Leu Gln Thr Leu Thr
        195                 200                 205

Met Thr Asn Ala Ala Thr Gln Pro Gly Thr Thr Ile Leu Gln Tyr
210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
                245                 250                 255

Ala Pro Thr Ser Thr Ile Ala Pro Gly Val Val Met Ala Ser Ser Pro
            260                 265                 270

Ala Leu Pro Thr Gln Pro Ala Glu Glu Ala Ala Arg Lys Arg Glu Val
        275                 280                 285

Arg Leu Met Lys Asn Arg Glu Ala Ala Arg Glu Cys Arg Arg Lys Lys
290                 295                 300

Lys Glu Tyr Val Lys Cys Leu Glu Asn Arg Val Ala Val Leu Glu Asn
305                 310                 315                 320

Gln Asn Lys Thr Leu Ile Glu Glu Leu Lys Ala Leu Lys Asp Leu Tyr
                325                 330                 335

Cys His Lys Ser Asp
            340

<210> SEQ ID NO 7
<211> LENGTH: 379
<212> TYPE: PRT
<213> ORGANISM: Homo sapiens

<400> SEQUENCE: 7

Met Ala Ala Ala Ala Gln Gly Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
```

```
                165                 170                 175
Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
    370                 375

<210> SEQ ID NO 8
<211> LENGTH: 360
<212> TYPE: PRT
<213> ORGANISM: Homo sapiens

<400> SEQUENCE: 8

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160
```

-continued

```
Cys Asp Leu Lys Ile Cys Asp Phe Gly Leu Ala Arg Val Ala Asp Pro
            165                 170                 175
Asp His Asp His Thr Gly Phe Leu Thr Glu Tyr Val Ala Thr Arg Trp
            180                 185                 190
Tyr Arg Ala Pro Glu Ile Met Leu Asn Ser Lys Gly Tyr Thr Lys Ser
        195                 200                 205
Ile Asp Ile Trp Ser Val Gly Cys Ile Leu Ala Glu Met Leu Ser Asn
        210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
            245                 250                 255
Asn Leu Lys Ala Arg Asn Tyr Leu Leu Ser Leu Pro His Lys Asn Lys
            260                 265                 270
Val Pro Trp Asn Arg Leu Phe Pro Asn Ala Asp Ser Lys Ala Leu Asp
            275                 280                 285
Leu Leu Asp Lys Met Leu Thr Phe Asn Pro His Lys Arg Ile Glu Val
        290                 295                 300
Glu Gln Ala Leu Ala His Pro Tyr Leu Glu Gln Tyr Tyr Asp Pro Ser
305                 310                 315                 320
Asp Glu Pro Ile Ala Glu Ala Pro Phe Lys Phe Asp Met Glu Leu Asp
            325                 330                 335
Asp Leu Pro Lys Glu Lys Leu Lys Glu Leu Ile Phe Glu Glu Thr Ala
            340                 345                 350
Arg Phe Gln Pro Gly Tyr Arg Ser
            355             360
```

US 7,427,485 B2

METHOD FOR CLASSIFICATION OF ANTI-PSYCHOTIC DRUGS

RELATED APPLICATIONS

This application claims benefit, under 35 U.S.C. §119(e), of U.S. provisional application No. 60/316,338, filed on Aug. 31, 2001, which is incorporated herein by reference in its entirety.

This invention was made with Government support under grant number MH 40899 awarded by the National Institute of Mental Health. The United States Government has certain rights in the invention.

1. TECHNICAL FIELD

The present invention relates to a method for identifying an agent to be tested for an ability to treat a psychotic disorder in a patient in need of such treatment. The invention also relates to a method for screening candidate drugs for anti-psychotic drug activity, preferably atypical anti-psychotic drug activity, comprising contacting cells or tissues with a candidate drug, determining levels of phosphorylation of the intracellular signaling proteins, DARPP-32, ERK1, ERK2 and CREB, in said cells or tissues and determining the pattern of the levels of phosphorylation of the proteins. In one aspect of the invention, the pattern of the levels of phosphorylation of DARPP-32, ERK1, ERK2 and CREB in response to a candidate drug is compared with the pattern of the levels of phosphorylation of DARPP-32, ERK1, ERK2 and CREB in response to a known atypical anti-psychotic drug.

2. BACKGROUND OF THE INVENTION

There are several important intracellular signaling proteins in brain tissue that have been linked to regulation of neurotransmitters that are involved in neurological diseases such as depression, schizophrenia, and Parkinson's disease. These intracellular signaling proteins include DARPP-32 (Dopamine- and cAMP-regulated phosphoprotein, Mr 32,000), ERK1 and ERK2 (extracellular signal-regulated protein kinases 1 and 2), and CREB cAMP-response element binding protein).

2.1. DARPP-32

DARPP-32 was discovered as a major target for dopamine (DA) and cAMP in the brain (Walaas et al. 1983. *Nature* 301:69-71). DARPP-32 is enriched in the two major projection areas for dopaminergic neurons, the prefrontal cortex and the striatum. DARPP-32 plays an obligatory role in the biochemical, electrophysiological, transcriptional, and behavioral effects of dopamine (Greengard, P. et al. 1999. *Neuron* 23:435-447). One study has linked the level of DARPP-32 with the pharmacological activity of certain anti-depressant compounds (Guitart, X. and E. J. Nestler. 1992. *J. Neurochem.* 59:1164-1167). These researchers demonstrated that chronic administration of lithium, imipramine, and tranylcypromine in rats produced significant increases in frontal cortex levels of DARPP-32 immunoreactivity, while administration of haloperidol, morphine, and cocaine were without effects on DARPP-32 immunoreactivity. Lithium is used for treatment of manic-depressive illness, while imipramine and tranylcypromine are anti-depressants. Imipramine acts by inhibiting norepinephrine re-uptake while tranylcypromine is a monoamine oxidase inhibitor.

2.2. cAMP Response Element Binding Protein (CREB)

In neurons, Ca2+ influx through different calcium channels activates distinct signaling pathways that either target the serum response element (SRE) or the calcium response element ("CaRE" or "CRE") within the c-fos promoter (Ghosh et al., J. Neurobiol March 1994;25(3):294-303). Transcription through the CRE requires the induced phosphorylation of the cAMP response element binding protein (CREB) at Ser133. CREB contains basic domain/leucine zipper motifs and binds as a dimer to CRE (De Cesare et al., Prog Nucleic Acid Res Mol Biol 2000;64:343-69). The activation function of CRE-binding proteins such as CREB is modulated by phosphorylation by several kinases and is mediated by coactivators such as CBP and p300 (De Cesare et al., Prog Nucleic Acid Res Mol Biol 2000;64:343-69)

Ca2+ thus regulates gene expression by multiple signaling pathways, including the one that involves the Ca(2+)-dependent phosphorylation of the transcription factor CREB (Ghosh et al., J Neurobiol March 1994;25(3):294-303). CREB is involved in the formation of memory in diverse organisms and regulates the formation of memories of various types of tasks that utilize different brain structures, including long-term memory (LTM) consolidation (Lamprecht, Cell Mol Life Sci April 1999;55(4):554-63; Huang et al., Essays Biochem 1998;33:165-78).

2.3. ERK1 and ERK2

Extracellular signal-regulated kinase 1 (ERK1) and Extracellular signal-regulated kinase 2 (ERK2) are part of the mitogen-activated protein kinase (MAP kinase, MAPK) superfamily. The MAPK superfamily of signaling cascades is a critical regulator of cell division and differentiation (Sweatt, 2001, J. Neurochem. (January) 76(1):1-10) and is also involved in learning and memory (Sweatt, 2001, J. Neurochem. (January) 76(1):1-10). The MAPK cascade is part of a family of signaling cascades that share the motif of three serially linked kinases regulating each other by sequential phosphorylation (Sweatt, 2001, J. Neurochem. (January) 76(1):1-10). The superfamily of MAPK signaling cascades includes the extracellular signal-regulated kinases (ERKs), the JNKs and the p38 stress activated protein kinases (Sweatt, 2001, J. Neurochem. (January) 76(1):1-10).

The most abundant ERKs in the brain are p44 MAPK (ERK1) and p42 MAPK (ERK2). ERK1 and ERK2 serve as intermediates that regulate serine/threonine phosphorylations in downstream intracellular signaling events (see, e.g., Boulton et al., 1991, Cell 65(4):663-75). ERKs are activated through phosphorylation at two sites, Thr202 and Tyr204 (for ERK1) and Thr185 and Tyr 187 (for ERK2).

ERKs are also abundantly expressed in neurons in the mature central nervous system, where the ERK signaling system has been apparently co-opted in mature neurons to function in synaptic plasticity and memory (Sweatt, 2001, J. Neurochem. (January) 76(1):1-10). ERKs also appear to serve as biochemical signal integrators and molecular coincidence detectors for coordinating responses to extracellular signals in neurons (Sweatt, 2001, J. Neurochem. (January) 76(1):1-10). ERK1 and ERK2 are involved in the induction of c-fos via phosphorylation and activation of CREB (Sweatt, 2001, J. Neurochem. (January) 76(1):1-10).

2.4. Classification of Anti-Psychotic Drugs

Anti-psychotic drugs have been classified into two classes: typical and atypical. Typical anti-psychotics include haloperidol, a drug that has been in use for over 30 years. The efficacy of the typical anti-psychotics is limited, however, and their side effects often limit their use as well. Such side effects include acute extrapyramidal effects such as acute dystonias (abnormal muscle spasms and postures), pseudoparkinsonism, and akathisia. Typical anti-psychotics appear to produce their pharmacological effects at least in part through acting as antagonists at the dopamine D2 receptor (see, e.g., Silverstone T., Acta Psychiatr Scand Suppl 1990;358:88-91).

Atypical anti-psychotics were developed in more recent years to overcome some of the limitations of the older typical anti-psychotic compounds. One such drug is clozapine, which is an improvement over drugs such as haloperidol, because it is almost devoid of extrapyramidal side effects. The mechanism of action of atypical anti-psychotics, however, is not well understood. The pharmaceutical industry has tried to develop other drugs with activity similar to clozapine, but development efforts have been hindered by the lack of understanding of the mechanism of action of such typical antipsychotics.

Anti-psychotic drugs are typically tested in animal models. However, no one model is predictive of clinical efficacy in controlling "positive" psychotic symptoms such as delusions and auditory hallucinations and "negative" symptoms such as flat affect and avolition. In recent years, "atypical" antipsychotics have come into wide use, predominantly because they provide the advantage of greatly reduced or nearly absent extrapyramidal side effects such as pseudoparkinsonism and other movement disorders. One such atypical antipsychotic, clozapine, has been shown to improve negative symptoms and is almost devoid of extrapyramidal side effects. Regular users of clozapine, however, are at risk for agranulocytosis, a lethal rupture of blood cells, and their white blood count must be continuously monitored via expensive laboratory tests. This adds considerably to the cost and limits the availability of this treatment.

Therefore, considerable effort has been expended to find an improved compound with similar antipsychotic properties. Hampered by the relative lack of insight into the mechanism of action of these drugs, investigators attempt to match candidate antipsychotics to clozapine using many different behavioural and biochemical parameters. For example, Millan et al. (2000, J Pharmacology and Experimental Therapeutics 292, 54-66) disclose the use of 14 different animal models and nine different receptor-binding assays to compare prospective antipsychotic compound S18327 (1-{2-[4-(6-Fluoro-1,2-benzisoxazol-3-yl)piperid-1-yl]ethyl}3-phenyl imidazolin-2-one) to clozapine.

Another test used to differentiate anti-psychotic drugs is comparison of their abilities to induce immediate-early gene c-fos. Typical and atypical anti-psychotics differently affect the expression of the immediate-early gene c-fos in the dorsal striatum, a region of the brain implicated in controlling movement (Robertson, G. S. et al. 1994. *J. Pharmacol. Exp. Ther.* 271:1058-1066). Haloperidol, a typical anti-psychotic, is much more effective at inducing c-fos expression as compared to clozapine, an atypical anti-psychotic (Robertson, G. S. et al. 1994. *J. Pharmacol. Exp. Ther.* 271:1058-1066). Studies have indicated that two mitogen-activated protein kinases, ERK1 and ERK2, are involved in the induction of c-fos via phosphorylation and activation of the transcription factor CREB (Sweatt, J. D. 2001. *J. Neurochem.* 76:1-10). Clozapine, on the other hand, has weak c-fos inductive activity in the dorsal striatum, but strongly induces c-fos expression in the medial prefrontal cortex. This action may be linked to the ability of clozapine to relieve negative psychotic symptoms. Once again, however, the mechanism underlying this induction is unclear.

Wettstein et al. (1999, Prog Neuropsychopharmacol Biol Psychiatry April;23(3):533-44) discloses that typical and atypical antipsychotic agents, as a drug class, effectively block the effects of the hallucinogen 1-[2,5-dimethoxy-4-iodophenyl]-2-aminopropane (DOI). DOI is an hallucinogen having high affinity and selectivity as an agonist at 5-HT2A/2C receptors. To identify an antipsychotic compound, the compound is assessed as an antagonist of DOI-induced behaviors in rats. DOI (0.3-10.0 mg/kg; i.p.) produces dose-related behavioral effects including head-and-body shakes, forepaw tapping and skin-jerks. Effects of antipsychotic drugs and other compounds (30 min pretreatment; i.p.) are examined against a fixed dose of DOI (3.0 mg/kg). M100907 (MDL100,907), risperidone, haloperidol, clozapine, iloperidone, olanzapine, amperozide, remoxipride, ritanserin and the neurotensin agonist NT1 (N alpha MeArg-Lys-Pro-Trp-Tle-Leu) antagonize each of the three behavioral effects of DOI. The drawback of this method, however, is that it does not distinguish between typical and atypical anti-psychotic drugs.

Other methods commonly used for identifying potential antipsychotic compounds include prepulse inhibition assays, such as the assays disclosed by Braff et al. (1992, Gating and habituation of the startle reflex in schizophrenic patients. Arch Gen Psychiatry 49:206-215) and by Swerdlow and Geyer (1993, Clozapine and haloperidol in an animal model of sensorimotor gating deficits in schizophrenia. Pharmacol Biochem Behav 44:741-744). Again, the drawback of these method is that they do not distinguish between typical and atypical anti-psychotic drugs. Also, an additional drawback of such behavioral tests is that they are labor intensive.

Surprisingly little is understood, however, about the mechanisms of action of atypical anti-psychotic drugs. Development efforts to develop other atypical anti-psychotic have been hindered by this lack of understanding.

Therefore, there is a need in the art to provide new methods of screening that can be used to develop novel compositions or drugs that can be used to treat psychotic diseases or disorders. Furthermore, there is a need for simple tests of intracellular consequences of antipsychotic action. Since all anti-psychotics act upon multiple receptors, with widely varying downstream effects in terms of both effective relief of symptoms and unwanted side effects, analysis of the intracellular integration of these signals provides a straightforward, cost-effective, and mechanism-based comparison useful for development of the next generation of therapeutic drugs. There is also a need to develop treatments for such diseases or disorders that are due, at least in part, to an aberration or dysregulation of an intracellular signaling pathway regulated by DARPP-32, ERK1, ERK2 and/or CREB. The present invention provides such methods and compositions.

Citation or identification of any reference in Section 2, or in any other section of this application, shall not be considered an admission that such reference is available as prior art to the present invention.

3. SUMMARY OF THE INVENTION

The invention provides a method for identifying an agent to be tested for an ability to treat a psychotic disorder in a patient in need of such treatment comprising the steps of:

(a) contacting, in a cell or tissue, a potential agent with Thr-75 dephosphorylated DARPP-32 and detecting the amount of phosphorylation of Thr-75 dephosphorylated DARPP-32, or (b) contacting, in a cell or tissue, the potential agent with Thr-75 phosphorylated DARPP-32 and detecting the amount of dephosphorylation of Thr-75 phosphorylated DARPP-32, or (c) contacting, in a cell or tissue, the potential agent with Thr202-dephosphorylated ERK1 and detecting the amount of phosphorylation of Thr202-dephosphorylated ERK1, or (d) contacting, in a cell or tissue, the potential agent with Thr202-phosphorylated ERK1 and detecting the amount of dephosphorylation of Thr202-phosphorylated ERK1, or (e) contacting, in a cell or tissue, the potential agent with Tyr204-dephosphorylated ERK1 and detecting the amount of phosphorylation of Tyr204-dephosphorylated ERK1, or (f) contacting, in a cell or tissue, the potential agent with Tyr204-phosphorylated ERK1 and detecting the amount of dephosphorylation of Tyr204-phosphorylated ERK1, or (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2, or (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2, or (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential atypical anti-psychotic compound if:

(i) an increase in the level of phosphorylation of Thr-75 dephosphorylated DARPP-32 is detected in step (a), or (ii) a decrease in the level of dephosphorylation of Thr-75 phosphorylated DARPP-32 is detected in step (b), or (iii) a decrease in the level of phosphorylation of Thr202-dephosphorylated ERK1 is detected in step (c), or (iv) an increase in the level of dephosphorylation of Thr202-phosphorylated ERK1 is detected in step (d), or (v) a decrease in the level of phosphorylation of Tyr204-dephosphorylated ERK1 is detected in step (e), or (vi) an increase in the level of dephosphorylation of Tyr204-phosphorylated ERK1 is detected in step (f), or (vii) a decrease in the level of phosphorylation of Thr185-dephosphorylated ERK2 is detected in step (g), or (viii) an increase in the level of dephosphorylation of Thr185-phosphorylated ERK2 is detected in step (h), or (ix) a decrease in the level of phosphorylation of Tyr187-dephosphorylated ERK2 is detected in step (i), or (x) an increase in the level of dephosphorylation of Tyr187-phosphorylated ERK2 is detected in step (j), or (xi) a decrease in the level of phosphorylation of Ser133-dephosphorylated CREB is detected in step (k), or (xii) an increase in the level of dephosphorylation of Ser133-phosphorylated CREB is detected in step (l), respectively, relative to a control level, in the presence of the potential agent.

In one embodiment, the invention provides a method comprising any one of steps (a)-(l).

In another embodiment, the invention provides a method comprising any two of steps (a)-(l).

In another embodiment, the invention provides a method comprising any three of steps (a)-(l).

In another embodiment, the invention provides a method comprising any four of steps (a)-(l).

In another embodiment, the invention provides a method comprising any five of steps (a)-(l).

In another embodiment, the invention provides a method comprising any six of steps (a)-(l).

In another embodiment, the invention provides a method comprising the additional steps of:

(m) contacting, in a cell or tissue, the potential agent with Thr34-dephosphorylated DARPP-32 and detecting the amount of phosphorylation of Thr34-dephosphorylated DARPP-32, or (n) contacting, in a cell or tissue, the potential agent with Thr34-phosphorylated DARPP-32 and detecting the amount of dephosphorylation of Thr34-phosphorylated DARPP-32, wherein the agent is identified as a potential atypical anti-psychotic compound if:

(xiii) an increase in the phosphorylation of Thr34-dephosphorylated DARPP-32 is detected in step (m), or (xix) a decrease in the dephosphorylation of Thr34-phosphorylated DARPP-32 is detected in step (n), relative to a control level, in the presence of the potential agent.

In another embodiment, the ability to treat a psychotic disorder is tested so that if the compound ameliorates the psychotic disorder, an atypical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

In another embodiment, the invention provides a method for identifying an agent to be tested for an ability to treat a psychotic disorder in a patient in need of such treatment comprising the steps of:

(a) contacting, in a cell or tissue, a potential agent with Thr-75 dephosphorylated DARPP-32 and detecting the amount of phosphorylation of Thr-75 dephosphorylated DARPP-32, or (b) contacting, in a cell or tissue, the potential agent with Thr-75 phosphorylated DARPP-32 and detecting the amount of dephosphorylation of Thr-75 phosphorylated DARPP-32; and (c) contacting, in a cell or tissue, the potential agent with Thr202-dephosphorylated ERK1 and detecting the amount of phosphorylation of Thr202-dephosphorylated ERK1, or (d) contacting, in a cell or tissue, the potential agent with Thr202-phosphorylated ERK1 and detecting the amount of dephosphorylation of Thr202-phosphorylated ERK1; and (e) contacting, in a cell or tissue, the potential agent with Tyr204-dephosphorylated ERK1 and detecting the amount of phosphorylation of Tyr204-dephosphorylated ERK1, or (f) contacting, in a cell or tissue, the potential agent with Tyr204-phosphorylated ERK1 and detecting the amount of dephosphorylation of Tyr204-phosphorylated ERK1; and (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2; and (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2; and (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential atypical anti-psychotic compound if:
(i) an increase in the level of phosphorylation of Thr-75 dephosphorylated DARPP-32 is detected in step (a), or
(ii) a decrease in the level of dephosphorylation of Thr-75 phosphorylated DARPP-32 is detected in step (b); and
(iii) a decrease in the level of phosphorylation of Thr202-dephosphorylated ERK1 is detected in step (c), or
(iv) an increase in the level of dephosphorylation of Thr202-phosphorylated ERK1 is detected in step (d); and
(v) a decrease in the level of phosphorylation of Tyr204-dephosphorylated ERK1 is detected in step (e), or
(vi) an increase in the level of dephosphorylation of Tyr204-phosphorylated ERK1 is detected in step (f); and
(vii) a decrease in the level of phosphorylation of Thr185-dephosphorylated ERK2 is detected in step (g), or
(viii) an increase in the level of dephosphorylation of Thr185-phosphorylated ERK2 is detected in step (h); and
(ix) a decrease in the level of phosphorylation of Tyr187-dephosphorylated ERK2 is detected in step (i), or
(x) an increase in the level of dephosphorylation of Tyr187-phosphorylated ERK2 is detected in step (j); and
(xi) a decrease in the level of phosphorylation of Ser133-dephosphorylated CREB is detected in step (k), or
(xii) an increase in the level of dephosphorylation of Ser133-phosphorylated CREB is detected in step (l), respectively, relative to a control level, in the presence of the potential agent.

In one embodiment, the method comprises the additional steps of:
(m) contacting, in a cell or tissue, the potential agent with Thr34-dephosphorylated DARPP-32 and detecting the amount of phosphorylation of Thr34-dephosphorylated DARPP-32, or (n) contacting, in a cell or tissue, the potential agent with Thr34-phosphorylated DARPP-32 and detecting the amount of dephosphorylation of Thr34-phosphorylated DARPP-32, wherein the agent is identified as a potential atypical anti-psychotic compound if:
(xiii) an increase in the phosphorylation of Thr34-dephosphorylated DARPP-32 is detected in step (m), or
(xix) a decrease in the dephosphorylation of Thr34-phosphorylated DARPP-32 is detected in step (n), relative to a control level, in the presence of the potential agent.

In one embodiment, the ability to treat a psychotic disorder is tested so that if the compound ameliorates the psychotic disorder, an atypical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

The invention further provides a method for identifying an agent to be tested for an ability to treat a psychotic disorder in a patient in need of such treatment comprising the steps of:
(a) contacting, in a cell or tissue, a potential agent with Thr-75 dephosphorylated DARPP-32 and detecting the amount of phosphorylation of Thr-75 dephosphorylated DARPP-32, or (b) contacting, in a cell or tissue, the potential agent with Thr-75 phosphorylated DARPP-32 and detecting the amount of dephosphorylation of Thr-75 phosphorylated DARPP-32, or (c) contacting, in a cell or tissue, the potential agent with Thr202-dephosphorylated ERK1 and detecting the amount of phosphorylation of Thr202-dephosphorylated ERK1, or (d) contacting, in a cell or tissue, the potential agent with Thr202-phosphorylated ERK1 and detecting the amount of dephosphorylation of Thr202-phosphorylated ERK1, or (e) contacting, in a cell or tissue, the potential agent with Tyr204-dephosphorylated ERK1 and detecting the amount of phosphorylation of Tyr204-dephosphorylated ERK1, or (f) contacting, in a cell or tissue, the potential agent with Tyr204-phosphorylated ERK1 and detecting the amount of dephosphorylation of Tyr204-phosphorylated ERK1, or (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2, or (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2, or (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential typical antipsychotic compound if:

(i) no change or a decrease in the level of phosphorylation of Thr-75 dephosphorylated DARPP-32 is detected in step (a), or (ii) no change or an increase in the level of dephosphorylation of Thr-75 phosphorylated DARPP-32 is detected in step (b), or (iii) an increase in the level of phosphorylation of Thr202-dephosphorylated ERK1 is detected in step (c), or (iv) a decrease in the level of dephosphorylation of Thr202-phosphorylated ERK1 is detected in step (d), or (v) an increase in the level of phosphorylation of Tyr204-dephosphorylated ERK1 is detected in step (e), or (vi) a decrease in the level of dephosphorylation of Tyr204-phosphorylated ERK1 is detected in step (f), or (vii) an increase in the level of phosphorylation of Thr185-dephosphorylated ERK2 is detected in step (g), or (viii) a decrease in the level of dephosphorylation of Thr185-phosphorylated ERK2 is detected in step (h), or (ix) an increase in the level of phosphorylation of Tyr187-dephosphorylated ERK2 is detected in step (i), or (x) a decrease in the level of dephosphorylation of Tyr187-phosphorylated ERK2 is detected in step (j), or (xi) an increase in the level of phosphorylation of Ser133-dephosphorylated CREB is detected in step (k), or (xii) a decrease in the level of dephosphorylation of Ser133-phosphorylated CREB is detected in step (l), respectively, relative to a control level, in the presence of the potential agent.

In one embodiment, the method comprises the additional steps of:

(m) contacting the potential agent with Thr34-dephosphorylated DARPP-32 and detecting the amount of phosphorylation of Thr34-dephosphorylated DARPP-32, or (n) contacting the potential agent with Thr34-phosphorylated DARPP-32 and detecting the amount of dephosphorylation of Thr34-phosphorylated DARPP-32, wherein the agent is identified as a potential typical antipsychotic compound if:

(xiii) an increase in the phosphorylation of Thr34-dephosphorylated DARPP-32 is detected in step (m), or (xix) a decrease in the dephosphorylation of Thr34-phosphorylated DARPP-32 is detected in step (n), relative to a control level, in the presence of the potential agent.

In another embodiment, the ability to treat a psychotic disorder is tested so that if the compound ameliorates the psychotic disorder, a typical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

In certain embodiments of the above-described methods for identifying agents as a potential atypical or typical antipsychotic compound, the level of phosphorylation or dephosphorylation is detected with a phosphospecific antibody.

In certain embodiments of the above-described methods for identifying agents as a potential atypical or typical antipsychotic compound, the level of phosphorylation or dephosphorylation is detected by measuring kinase activity.

In certain embodiments of the above-described methods for identifying agents as a potential atypical or typical antipsychotic compound, the level of phosphorylation or dephosphorylation is detected by measuring phosphatase activity.

In certain embodiments of the above-described methods for identifying agents as a potential atypical or typical antipsychotic compound, the cell or tissue is a human cell or human tissue.

In certain embodiments of the above-described methods for identifying agents as a potential atypical or typical antipsychotic compound, the cell or tissue is a cell.

In certain embodiments of the above-described methods for identifying agents as a potential atypical or typical antipsychotic compound, the cell or tissue is a tissue.

In certain embodiments of the above-described methods for identifying agents as a potential atypical or typical antipsychotic compound, the cell or tissue is a whole animal.

In certain embodiments of the above-described methods for identifying agents as a potential atypical or typical antipsychotic compound, the cell or tissue is a human.

In certain embodiments of the above-described methods for identifying agents as a potential atypical or typical antipsychotic compound, DARPP-32 is human DARPP-32.

In certain embodiments of the above-described methods for identifying agents as a potential atypical or typical antipsychotic compound, CREB is human CREB.

In certain embodiments of the above-described methods for identifying agents as a potential atypical or typical antipsychotic compound, ERK1 is human ERK1.

In certain embodiments of the above-described methods for identifying agents as a potential atypical or typical antipsychotic compound, ERK2 is human ERK2.

In certain embodiments of the above-described methods for identifying agents as a potential atypical or typical antipsychotic compound, DARPP-32 is mouse DARPP-32.

In certain embodiments of the above-described methods for identifying agents as a potential atypical or typical antipsychotic compound, CREB is mouse CREB.

In certain embodiments of the above-described methods for identifying agents as a potential atypical or typical antipsychotic compound, ERK1 is mouse ERK1.

In certain embodiments of the above-described methods for identifying agents as a potential atypical or typical antipsychotic compound, ERK2 is mouse ERK2.

In another embodiment, the invention also provides a computer system for identifying an agent to be tested for an ability to treat a psychotic disorder in a patient in need of such treatment, the computer system comprising a processor, and a memory encoding one or more programs coupled to the processor, wherein the one or more programs cause the processor to perform any one of the above-described methods for identifying agents as a potential atypical or typical anti-psychotic compound. In certain embodiments, the computer system comprises a database that includes a plurality of records containing information relating to phosphorylation patterns observed for particular potential compounds of interest.

3.1. Definitions

As used herein, the term "modulate" or "modulation" shall have its usual meaning, and encompasses the meanings of the words "enhance," "inhibit," and "mimic." "Modulation" of activity may be either an increase or a decrease in activity.

As used herein, an "agonist" is any compound that acts directly or indirectly through or upon a receptor to produce a pharmacological effect, while an "antagonist" is any compound that blocks the stimulation of a receptor and its resulting pharmacological effect.

As used herein, an "effective amount" of a modulatory compound is an amount that can be determined by one of skill in the art based on data from studies using methods of analysis such as those disclosed herein. Such data may include, but not be limited to, results from IC50 determinations, as discussed hereinbelow.

As used herein, the term "DARPP-32" is used interchangeably with "Dopamine- and cyclic AMP (cAMP)-Regulated PhosphoProtein" and "DARPP32" and is a 32 kilodalton cytosolic protein that is selectively enriched in medium-sized spiny neurons in neostriatum. The human, mouse, rat and bovine DARPP-32 amino acid sequences are disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties (see SEQ ID NOS: 1-4, respectively).

As used herein, the term "Thr75 DARPP-32" is used interchangeably with "Thr75 DARPP32," "thr$^{75}$ DARPP-32", "Threonine-75 DARPP-32" and "threonine-75 DARPP-32" along with analogous abbreviations. In one embodiment, it denotes the seventy-fifth amino acid residue in the amino acid sequence of DARPP-32 as disclosed by Brene et al. (J. Neurosci. 14:985-998 (1994)) having the GenBank Accession of AAB30129.1, which is a threonine residue that, as disclosed herein, can be phosphorylated by Cdk5 (see, e.g., Greengard et al., Neuron 23:435-447 (1999); Bibb et al., Proc. Natl. Acad. Sci. 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of identifying Agents That Regulate Phosphorylation/Dephosphorylation in Dopamine Signaling," filed Oct. 13, 2000, each of which is incorporated herein by reference in its entirety).

As used herein, the term "Thr75DARPP-32" denotes the seventy-fifth amino acid residue in the amino acid sequence of human DARPP-32. Unless otherwise indicated, the term can also refer to a corresponding amino acid residue in the DARPP-32 from another species, e.g., murine, bovine, etc. These sequences are well-known to one of skill in the art, and using routine methods, the corresponding amino acid residue can be identified.

As used herein, the term "phospho-Thr75 DARPP-32," or analogous abbreviations as disclosed above, denotes the phosphorylated form of Thr75 DARPP-32.

As used herein, the term "Thr34 DARPP-32" is used interchangeably with "Thr34 DARPP32," "thr$^{34}$ DARPP-32" 'Threonine-34 DARPP-32" and "threonine-34 DARPP-32" along with analogous abbreviations. In one embodiment, it denotes the thirty-fourth amino acid residue of the amino acid sequence of DARPP-32 as disclosed by Brene et al. (J. Neurosci. 14:985-998 (1994)) having the GenBank Accession No. of AAB30129.1, which is a threonine residue that can be phosphorylated by the cyclic AMP dependent protein kinase (PKA) (see, e.g., Greengard et al., Neuron 23:435-447 (1999); Bibb et al., Proc. Natl. Acad. Sci. 97:6809-68 14 (2000); and U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "Thr34DARPP-32" denotes the thirty-fourth amino acid residue in the amino acid sequence of human DARPP-32. Unless otherwise indicated, the term can also refer to a corresponding amino acid residue in the DARPP-32 from another species, e.g., murine, bovine, etc. These sequences are well-known to one of skill in the art, and using routine methods, the corresponding amino acid residue can be identified.

As used herein, the term "phospho-Thr34 DARPP-32," or analogous abbreviations as disclosed above, denotes the phosphorylated form of Thr34 DARPP-32.

As used herein, the term CREB is used interchangeably with "cAMP response element binding protein." CREB includes, but is not limited to members of the CREB family. Transcription through the calcium response element (CRE) requires the induced phosphorylation of the cAMP response element binding protein (CREB) at Ser133.

As used herein, "an analog of CREB" is used interchangeably with "a homolog of CREB" and is a binding protein that, like CREB, binds to the CRE and is activated by phosphorylation at a serine corresponding to Ser133 of CREB.

As used herein, the term "Ser133 CREB" is used interchangeably with "Serine 133 CREB" and with analogous abbreviations. In one embodiment, it denotes the one-hundred-and-thirty-third amino acid residue of the amino acid sequence of human CREB as disclosed by Hoeffler et al. (1988, Cyclic AMP-responsive DNA-binding protein: structure based on a cloned placental cDNA, Science 242 (4884), 1430-1433) (SEQ ID NO: 6) having the GenBank Accession No. of NP_604391, which is a serine residue that can be phosphorylated by PKA or calcium-calmodulin dependent protein kinases.

As used herein, the term "Ser133 CREB" denotes the one-hundred-and-thirty-third amino acid residue of the amino acid sequence of human CREB. Unless otherwise indicated, the term can also refer to a corresponding amino acid residue in the CREB from another species, e.g., murine, bovine, etc. These sequences are well-known to one of skill in the art, and using routine methods, the corresponding amino acid residue can be identified.

As used herein, the term "phospho-Ser133 CREB," or analogous abbreviations as disclosed above, denotes the phosphorylated form of Ser133 CREB.

As used herein, the term ERK1 is used interchangeably with "ERK-1" and "Extracellular signal-regulated kinase 1." ERK1 includes, but is not limited to members of the ERK1 (p44-MAPK) family. ERK1 is activated through phosphorylation at two sites, Thr202 and Tyr204.

As used herein, "an analog of ERK1" is used interchangeably with "a homolog of ERK1" and is an extracellular signal-regulated kinase, that like ERK1, is activated by phosphorylation at a threonine corresponding to Thr202 and a tyrosine corresponding to Tyr204 of ERK 1 and induces c-fos via phosphorylation and activation of the transcription factor CREB.

As used herein, the term "Thr202 ERK1" is used interchangeably with "Threonine 202 ERK1" and with analogous abbreviations. In one embodiment, it denotes the two-hundred-and-second amino acid residue of the amino acid sequence of human ERK1 as disclosed by Charest et al. (1993, Molecular cloning, expression, and characterization of the human mitogen-activated protein kinase p44erk1, Mol. Cell. Biol. 13 (8), 4679-4690) (SEQ ID NO: 7) having the GenBank Accession No. of P27361, which is a threonine residue that can be phosphorylated by MAP kinase/ERK Kinase 1 ("MEK1").

As used herein, the term "Thr202 ERK1" denotes the two-hundred-and-second amino acid residue of the amino acid sequence of human ERK1. Unless otherwise indicated, the term can also refer to a corresponding amino acid residue in the ERK1 from another species, e.g., murine, bovine, etc. These sequences are well-known to one of skill in the art, and using routine methods, the corresponding amino acid residue can be identified.

As used herein, the term "phospho-Thr202 ERK1," or analogous abbreviations as disclosed above, denotes the phosphorylated form of Thr202 ERK1.

As used herein, the term "Tyr204 ERK1" is used interchangeably with "Tyrosine 204 ERK1" and with analogous abbreviations. In one embodiment, it denotes the two-hundred-and-fourth amino acid residue of the amino acid sequence of ERK1 as disclosed by Charest et al. (1993, Molecular cloning, expression, and characterization of the human mitogen-activated protein kinase p44erk1, Mol. Cell. Biol. 13 (8), 4679-4690) (SEQ ID NO: 7) having the GenBank Accession No. of P27361, which is a threonine residue that can be phosphorylated by MAP kinase/ERK Kinase 1 ("MEK1").

As used herein, the term "Tyr204 ERK1" denotes the two-hundred-and-fourth amino acid residue of the amino acid sequence of human ERK1. Unless otherwise indicated, the term can also refer to a corresponding amino acid residue in the ERK1 from another species, e.g., murine, bovine, etc. These sequences are well-known to one of skill in the art, and using routine methods, the corresponding amino acid residue can be identified.

As used herein, the term "phospho-Tyr204 ERK1," or analogous abbreviations as disclosed above, denotes the phosphorylated form of Tyr204 ERK1.

As used herein, the term ERK2 is used interchangeably with "ERK-2" and "Extracellular signal-regulated kinase 2." ERK2 includes, but is not limited to members of the ERK2 family. ERK2 is activated through phosphorylation at two sites, Thr185 and Tyr187.

As used herein, "an analog of ERK2" is used interchangeably with "a homolog of ERK2" and is an extracellular signal-regulated kinase, that like ERK2, is activated by phosphorylation at a threonine corresponding to Thr185 and a tyrosine corresponding to Tyr187 of ERK2 and induces c-fos via phosphorylation and activation of the transcription factor CREB.

As used herein, the term "Thr185 ERK2" is used interchangeably with "Threonine 185 ERK2" and with analogous abbreviations. In one embodiment, it denotes the one-hundred and eighty-fifth amino acid residue of the amino acid sequence of ERK2 as disclosed by Boulton et al. (1991, ERKs: a family of protein-serine/threonine kinases that are activated and tyrosine phosphorylated in response to insulin and NGF, Cell 65 (4), 663-675) (SEQ ID NO: 8) having the GenBank Accession No. of NP_620407, which is a threonine residue that can be phosphorylated by MAP kinase/ERK Kinase 2 ("MEK2").

As used herein, the term "Thr185 ERK2" it denotes the one-hundred and eighty-fifth amino acid residue of the amino acid sequence of human ERK2. Unless otherwise indicated, the term can also refer to a corresponding amino acid residue in the ERK2 from another species, e.g., murine, bovine, etc. These sequences are well-known to one of skill in the art, and using routine methods, the corresponding amino acid residue can be identified.

As used herein, the term "phospho-Thr185 ERK2," or analogous abbreviations as disclosed above, denotes the phosphorylated form of Thr85 ERK2.

As used herein, the term "Tyr187 ERK2" is used interchangeably with "Tyrosine 187 ERK2" and with analogous abbreviations. In one embodiment, it denotes the one-hundred and eighty-seventh amino acid residue of the amino acid sequence of ERK2 as disclosed by Boulton et al. (1991, ERKs: a family of protein-serine/threonine kinases that are activated and tyrosine phosphorylated in response to insulin and NGF, Cell 65 (4), 663-675) (SEQ ID NO: 8) having the GenBank Accession No. of NP_620407, which is a tyrosine residue that can be phosphorylated by MAP kinase/ERK Kinase 2 ("MEK2").

As used herein, the term "Tyr187 ERK2" it denotes the one-hundred and eighty-seventh amino acid residue of the amino acid sequence of human ERK2. Unless otherwise indicated, the term can also refer to a corresponding amino acid residue in the ERK2 from another species, e.g., murine, bovine, etc. These sequences are well-known to one of skill in the art, and using routine methods, the corresponding amino acid residue can be identified.

As used herein, the term "phospho-Tyr187 ERK2," or analogous abbreviations as disclosed above, denotes the phosphorylated form of Tyr187 ERK2.

As used herein, the amount and/or rate of phosphorylation of DARPP-32 (or of a phosphorylatable fragment of DARPP-32), ERK1 (or of a phosphorylatable fragment of ERK1), ERK2 (or of a phosphorylatable fragment of ERK2) or CREB (or of a phosphorylatable fragment of CREB) as described hereinabove, in a kinase reaction is "significantly changed" when the amount and/or rate of phosphorylation DARPP-32 (or of a phosphorylatable fragment of DARPP-32), ERK1 (or of a phosphorylatable fragment of ERK1), ERK2 (or of a phosphorylatable fragment of ERK12), or CREB (or of a phosphorylatable fragment of CREB), respectively, is increased or decreased by a statistically significant amount, as determined by statistical methods commonly known in the art or by those statistical methods disclosed hereinbelow, relative to the control reaction. Preferably, a significant change in rate of the phosphorylation of DARPP-32 (or of a phosphorylatable fragment of DARPP-32), ERK1 (or of a phosphorylatable fragment of ERK1), ERK2 (or of a phosphorylatable fragment of ERK12), or CREB (or of a phosphorylatable fragment of CREB) observed in the presence of a potential modulator is at some point correlated with the Michaelis constants (e.g., the Vmax or Km) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the amount and/or rate of dephosphorylation of DARPP-32 (or of a phosphorylatable fragment of DARPP-32), ERK1 (or of a phosphorylatable fragment of ERK1), ERK2 (or of a phosphorylatable fragment of ERK2) or CREB (or of a phosphorylatable fragment of CREB), as described hereinabove, in a phosphatase reaction is "significantly changed" when the amount and/or rate of dephosphorylation DARPP-32 (or of a phosphorylatable fragment of DARPP-32), ERK1 (or of a phosphorylatable fragment of ERK1), ERK2 (or of a phosphorylatable fragment of ERK2) or CREB (or of a phosphorylatable fragment of CREB) is increased or decreased by a statistically significant amount, as determined by statistical methods commonly known in the art or by those statistical methods disclosed hereinbelow, relative to the control reaction. Preferably, a significant change in rate of the dephosphorylation of DARPP-32 by a molecule of interest (e.g., PP2C, PP2B or PP2A) observed in the presence of a potential modulator is at some point correlated with the Michaelis constants (e.g., the Vmax or Km) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the term "phosphorylatable fragment" of an intracellular signaling molecule, e.g., DARPP-32, ERK1, ERK2 or CREB, is a protein fragment of the molecule that contains a phosphorylatable residue, that, when in the dephosphorylated form, can be phosphorylated by a kinase. Such fragments can be between about 5 and 100 residues, or more preferably between about 10 and 50 residues. For example, in a particular embodiment, a phosphorylatable fragment of DARPP-32 comprises 5 consecutive amino acids from SEQ ID NO: 1 including Thr34. In another embodiment of this type, the peptide fragment comprises 7 consecutive amino acids from SEQ ID NO: 1 including Thr 34. In an alternative embodiment the peptide fragment comprises between 10 and 25 consecutive amino acids from SEQ ID NO: 1 including Thr34.

It will be apparent to one of skill in the art that phosphorylatable fragments of DARPP-32 (comprising a phospho-Thr75), ERK1 (comprising a phospho-Thr202 and/or a phospho-Tyr204), ERK2 (comprising a phospho-Thr185 and/or a phospho-Tyr187) and/or CREB (comprising a phospho-Ser133) may be similarly constructed.

All of the peptide fragments contemplated by the invention can be part of fusion peptides or proteins. According to the invention, a phosphorylatable fragment of an intracellular signaling molecule, e.g., DARPP-32, ERK1, ERK2 or CREB, can be prepared by any method commonly known in the art, e.g., cleaving (such as with a protease) and dephosphorylating a phosphorylated fragment from a larger fragment of a phosphorylated protein or from the full-length phosphorylated protein. Thus the fragments can be synthesized by either standard peptide synthesis disclosed below, or generated through recombinant DNA technology or by classical proteolysis.

As used herein, the term "psychotic disorder" is used interchangeably with the terms "psychosis," "psychotic condition," or analogous terms. A psychotic disorder includes, but is not limited to, psychotic depression, postpartum depression, affective disorder, schizoaffective disorder, schizophreniform disorder, schizophrenia, delusional disorder, brief psychotic disorder, shared psychotic disorder, borderline personality disorder, manic-depressive disorder, obsessive-compulsive disorder, Huntington's Disease, Tourette's syndrome and tic disorder.

As used herein, a "small organic molecule" is an organic compound (or organic compound complexed with an inorganic compound (e.g., metal) that has a molecular weight of less than 3 kilodaltons, preferably less than 1.5 kilodaltons. Preferably, the small organic molecule can cross the blood-brain barrier.

As used herein, the term "about" means within 10 to 15%, preferably within 5 to 10%. For example an amino acid sequence that contains about 60 amino acid residues can contain between 51 to 69 amino acid residues, more preferably 57 to 63 amino acid residues.

4. DETAILED DESCRIPTION OF THE INVENTION

The present invention is based on the surprising discovery that typical and atypical anti-psychotic drugs differentially affect the phosphorylation state of intracellular signaling proteins including DARPP-32, CREB and ERK1 and ERK2. This differential phosphorylation pattern can be used in methods to screen, classify and identify candidate atypical anti-psychotic drugs during drug development.

For clarity of disclosure, and not by way of limitation, the detailed description of the invention is divided into the subsections which follow.

4.1. Methods for Screening for Compounds that Modulate the Phosphorylation Patterns of DARPP-32, ERK1, ERK2 and CREB In one embodiment, the invention provides a method for screening candidate drugs for atypical anti-psychotic drug activity comprising contacting cells or tissues with a candidate drug, determining levels of phosphorylation of the intracellular signaling proteins, DARPP-32, ERK1, ERK2 and CREB, in said cells or tissues and determining the pattern of the levels of phosphorylation of the proteins. The pattern of the levels of phosphorylation of DARPP-32, ERK1, ERK2 and CREB is, in certain embodiments, compared with the pattern of the levels of phosphorylation of DARPP-32, ERK1, ERK2 and CREB in the presence of an atypical anti-psychotic drug. An atypical anti-psychotic drug includes, but is not limited to clozapine, risperidone, iloperidone, olanzapine, quetiapine zotepine, perospirone and ziprasidone.

The present invention provides, in vivo, in situ, and in vitro, methods of identifying an agent, drug or compound to be tested for an ability to treat a psychotic disorder in a patient in need of such treatment. Such methods can be used alone or in conjunction with each other. In a preferred embodiment, the invention provides methods for identifying a candidate atypical anti-psychotic drug.

The invention provides a method for identifying an agent to be tested for an ability to treat a psychotic disorder in a patient in need of such treatment comprising the steps of:

(a) contacting, in a cell or tissue, a potential agent with Thr-75 dephosphorylated DARPP-32 and detecting the amount of phosphorylation of Thr-75 dephosphorylated DARPP-32, or (b) contacting, in a cell or tissue, the potential agent with Thr-75 phosphorylated DARPP-32 and detecting the amount of dephosphorylation of Thr-75 phosphorylated DARPP-32, or (c) contacting, in a cell or tissue, the potential agent with Thr202-dephosphorylated ERK1 and detecting the amount of phosphorylation of Thr202-dephosphorylated ERK1, or (d) contacting, in a cell or tissue, the potential agent with Thr202-phosphorylated ERK1 and detecting the amount of dephosphorylation of Thr202-phosphorylated ERK1, or (e) contacting, in a cell or tissue, the potential agent with Tyr204-dephosphorylated ERK1 and detecting the amount of phosphorylation of Tyr204-dephosphorylated ERK1, or (f) contacting, in a cell or tissue, the potential agent with Tyr204-phosphorylated ERK1 and detecting the amount of dephosphorylation of Tyr204-phosphorylated ERK1, or (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2, or (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2, or (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential atypical anti-psychotic compound if:
(i) an increase in the level of phosphorylation of Thr-75 dephosphorylated DARPP-32 is detected in step (a), or
(ii) a decrease in the level of dephosphorylation of Thr-75 phosphorylated DARPP-32 is detected in step (b), or
(iii) a decrease in the level of phosphorylation of Thr202-dephosphorylated ERK1 is detected in step (c), or
(iv) an increase in the level of dephosphorylation of Thr202-phosphorylated ERK1 is detected in step (d), or
(v) a decrease in the level of phosphorylation of Tyr204-dephosphorylated ERK1 is detected in step (e), or
(vi) an increase in the level of dephosphorylation of Tyr204-phosphorylated ERK1 is detected in step (j), or
(vii) a decrease in the level of phosphorylation of Thr185-dephosphorylated ERK2 is detected in step (g), or
(viii) an increase in the level of dephosphorylation of Thr185-phosphorylated ERK2 is detected in step (h), or
(ix) a decrease in the level of phosphorylation of Tyr187-dephosphorylated ERK2 is detected in step (i), or
(x) an increase in the level of dephosphorylation of Tyr187-phosphorylated ERK2 is detected in step (j), or
(xi) a decrease in the level of phosphorylation of Ser133-dephosphorylated CREB is detected in step (k), or
(xii) an increase in the level of dephosphorylation of Ser133-phosphorylated CREB is detected in step (l), respectively, relative to a control level, in the presence of the potential agent.

In one embodiment, the invention provides a method comprising any one of steps (a)-(l).

In another embodiment, the invention provides a method comprising any two of steps (a)-(l).

In another embodiment, the invention provides a method comprising any three of steps (a)-(l).

In another embodiment, the invention provides a method comprising any four of steps (a)-(l).

In another embodiment, the invention provides a method comprising any five of steps (a)-(l).

In another embodiment, the invention provides a method comprising any six of steps (a)-(l).

In another embodiment, the invention provides a method comprising the additional steps of:
(m) contacting, in a cell or tissue, the potential agent with Thr34-dephosphorylated DARPP-32 and detecting the amount of phosphorylation of Thr34-dephosphorylated DARPP-32, or
(n) contacting, in a cell or tissue, the potential agent with Thr34-phosphorylated DARPP-32 and detecting the amount of dephosphorylation of Thr34-phosphorylated DARPP-32, wherein the agent is identified as a potential atypical anti-psychotic compound if:
(xiii) an increase in the phosphorylation of Thr34-dephosphorylated DARPP-32 is detected in step (m), or
(xix) a decrease in the dephosphorylation of Thr34-phosphorylated DARPP-32 is detected in step (n), relative to a control level, in the presence of the potential agent.

In another embodiment, the ability to treat a psychotic disorder is tested so that if the compound ameliorates the psychotic disorder, an atypical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

In another embodiment, the invention provides a method for identifying an agent to be tested for an ability to treat a psychotic disorder in a patient in need of such treatment comprising the steps of:
(a) contacting, in a cell or tissue, a potential agent with Thr-75 dephosphorylated DARPP-32 and detecting the amount of phosphorylation of Thr-75 dephosphorylated DARPP-32, or
(b) contacting, in a cell or tissue, the potential agent with Thr-75 phosphorylated DARPP-32 and detecting the amount of dephosphorylation of Thr-75 phosphorylated DARPP-32; and
(c) contacting, in a cell or tissue, the potential agent with Thr202-dephosphorylated ERK1 and detecting the amount of phosphorylation of Thr202-dephosphorylated ERK1, or
(d) contacting, in a cell or tissue, the potential agent with Thr202-phosphorylated ERK1 and detecting the amount of dephosphorylation of Thr202-phosphorylated ERK1; and
(e) contacting, in a cell or tissue, the potential agent with Tyr204-dephosphorylated ERK1 and detecting the amount of phosphorylation of Tyr204-dephosphorylated ERK1, or
(f) contacting, in a cell or tissue, the potential agent with Tyr204-phosphorylated ERK1 and detecting the amount of dephosphorylation of Tyr204-phosphorylated ERK1; and (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2; and (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2; and (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential atypical antipsychotic compound if:

(i) an increase in the level of phosphorylation of Thr-75 dephosphorylated DARPP-32 is detected in step (a), or (ii) a decrease in the level of dephosphorylation of Thr-75 phosphorylated DARPP-32 is detected in step (b); and (iii) a decrease in the level of phosphorylation of Thr202-dephosphorylated ERK1 is detected in step (c), or (iv) an increase in the level of dephosphorylation of Thr202-phosphorylated ERK1 is detected in step (d); and (v) a decrease in the level of phosphorylation of Tyr204-dephosphorylated ERK1 is detected in step (e), or (vi) an increase in the level of dephosphorylation of Tyr204-phosphorylated ERK1 is detected in step (f); and (vii) a decrease in the level of phosphorylation of Thr185-dephosphorylated ERK2 is detected in step (g), or (viii) an increase in the level of dephosphorylation of Thr185-phosphorylated ERK2 is detected in step (h); and (ix) a decrease in the level of phosphorylation of Tyr187-dephosphorylated ERK2 is detected in step (i), or (x) an increase in the level of dephosphorylation of Tyr187-phosphorylated ERK2 is detected in step (j); and (xi) a decrease in the level of phosphorylation of Ser133-dephosphorylated CREB is detected in step (k), or (xii) an increase in the level of dephosphorylation of Ser133-phosphorylated CREB is detected in step (l), respectively, relative to a control level, in the presence of the potential agent.

In one embodiment, the method comprises the additional steps of:

(m) contacting, in a cell or tissue, the potential agent with Thr34-dephosphorylated DARPP-32 and detecting the amount of phosphorylation of Thr34-dephosphorylated DARPP-32, or (n) contacting, in a cell or tissue, the potential agent with Thr34-phosphorylated DARPP-32 and detecting the amount of dephosphorylation of Thr34-phosphorylated DARPP-32, wherein the agent is identified as a potential atypical antipsychotic compound if:

(xiii) an increase in the phosphorylation of Thr34-dephosphorylated DARPP-32 is detected in step (m), or (xix) a decrease in the dephosphorylation of Thr34-phosphorylated DARPP-32 is detected in step (n), relative to a control level, in the presence of the potential agent.

In one embodiment, the ability to treat a psychotic disorder is tested so that if the compound ameliorates the psychotic disorder, an atypical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

The invention further provides a method for identifying an agent to be tested for an ability to treat a psychotic disorder in a patient in need of such treatment comprising the steps of:

(a) contacting, in a cell or tissue, a potential agent with Thr-75 dephosphorylated DARPP-32 and detecting the amount of phosphorylation of Thr-75 dephosphorylated DARPP-32, or (b) contacting, in a cell or tissue, the potential agent with Thr-75 phosphorylated DARPP-32 and detecting the amount of dephosphorylation of Thr-75 phosphorylated DARPP-32, or (c) contacting, in a cell or tissue, the potential agent with Thr202-dephosphorylated ERK1 and detecting the amount of phosphorylation of Thr202-dephosphorylated ERK1, or (d) contacting, in a cell or tissue, the potential agent with Thr202-phosphorylated ERK1 and detecting the amount of dephosphorylation of Thr202-phosphorylated ERK1, or (e) contacting, in a cell or tissue, the potential agent with Tyr204-dephosphorylated ERK1 and detecting the amount of phosphorylation of Tyr204-dephosphorylated ERK1, or (f) contacting, in a cell or tissue, the potential agent with Tyr204-phosphorylated ERK1 and detecting the amount of dephosphorylation of Tyr204-phosphorylated ERK1, or (g) contacting, in a cell or tissue, the potential agent with Thr185-dephosphorylated ERK2 and detecting the amount of phosphorylation of Thr185-dephosphorylated ERK2, or (h) contacting, in a cell or tissue, the potential agent with Thr185-phosphorylated ERK2 and detecting the amount of dephosphorylation of Thr185-phosphorylated ERK2, or (i) contacting, in a cell or tissue, the potential agent with Tyr187-dephosphorylated ERK2 and detecting the amount of phosphorylation of Tyr187-dephosphorylated ERK2, or (j) contacting, in a cell or tissue, the potential agent with Tyr187-phosphorylated ERK2 and detecting the amount of dephosphorylation of Tyr187-phosphorylated ERK2, or (k) contacting, in a cell or tissue, the potential agent with Ser133-dephosphorylated CREB and detecting the amount of phosphorylation of Ser133-dephosphorylated CREB, or (l) contacting, in a cell or tissue, the potential agent with Ser133-phosphorylated CREB and detecting the amount of dephosphorylation of Ser133-phosphorylated CREB, wherein the agent is identified as a potential typical antipsychotic compound if:

(i) no change or a decrease in the level of phosphorylation of Thr-75 dephosphorylated DARPP-32 is detected in step (a), or (ii) no change or an increase in the level of dephosphorylation of Thr-75 phosphorylated DARPP-32 is detected in step (b), or (iii) an increase in the level of phosphorylation of Thr202-dephosphorylated ERK1 is detected in step (c), or (iv) a decrease in the level of dephosphorylation of Thr202-phosphorylated ERK1 is detected in step (d), or (v) an increase in the level of phosphorylation of Tyr204-dephosphorylated ERK1 is detected in step (e), or (vi) a decrease in the level of dephosphorylation of Tyr204-phosphorylated ERK1 is detected in step (f), or (vii) an increase in the level of phosphorylation of Thr185-dephosphorylated ERK2 is detected in step (g), or (viii) a decrease in the level of dephosphorylation of Thr185-phosphorylated ERK2 is detected in step (h), or (ix) an increase in the level of phosphorylation of Tyr187-dephosphorylated ERK2 is detected in step (i), or (x) a decrease in the level of dephosphorylation of Tyr187-phosphorylated ERK2 is detected in step (j), or (xi) an increase in the level of phosphorylation of Ser133-dephosphorylated CREB is detected in step (k), or (xii) a decrease in the level of dephosphorylation of Ser133-phosphorylated CREB is detected in step (l), respectively, relative to a control level, in the presence of the potential agent.

In one embodiment, the method comprises the additional steps of:

(m) contacting the potential agent with Thr34-dephosphorylated DARPP-32 and detecting the amount of phosphorylation of Thr34-dephosphorylated DARPP-32, or (n) contacting the potential agent with Thr34-phosphorylated DARPP-32 and detecting the amount of dephosphorylation of Thr34-phosphorylated DARPP-32, wherein the agent is identified as a potential typical antipsychotic compound if:

(xiii) an increase in the phosphorylation of Thr34-dephosphorylated DARPP-32 is detected in step (m), or (xix) a decrease in the dephosphorylation of Thr34-phosphorylated DARPP-32 is detected in step (n), relative to a control level, in the presence of the potential agent.

In another embodiment, the ability to treat a psychotic disorder is tested so that if the compound ameliorates the psychotic disorder, a typical anti-psychotic compound is identified. In another embodiment, the psychotic disorder is schizophrenia. In another embodiment, the ability to treat a psychotic disorder is tested in a schizophrenic animal model.

In another embodiment, the detecting steps are performed at least 15 minutes and no longer than 30 minutes after the contacting steps.

In another embodiment, the detecting steps are performed at least 30 minutes and no longer than 60 minutes after the contacting steps.

In another embodiment, the detecting steps are performed 60 minutes after the contacting steps.

In another embodiment, the invention provides a method for classifying drugs with unknown pharmacological activity comprising contacting cells or tissues in vitro or in vivo with a drug with unknown pharmacological activity, determining levels of phosphorylation of proteins in said cells or tissues, and comparing the pattern of the levels of phosphorylation of the proteins with the pattern of the levels of phosphorylation of the proteins in the presence of drugs with known patterns of phosphorylation and known pharmacological activity, wherein identification of a similar pattern of phosphorylation of the unknown drug with a pattern of phosphorylation of a drug with known pharmacological activity results in classification of the unknown drug.

According to the invention, a cell or tissue may include, but not be limited to: an excitable cell, e.g., a sensory neuron, motorneuron, or interneuron; a glial cell; a primary culture of neuronal or glial cells; cell(s) derived from a neuronal or glial cell line; dissociated cell(s); whole cell(s); permeabilized cell(s); a cellular extract or purified enzyme preparation; and a tissue or organ, e.g., brain, brain structure, brain slice, spinal cord, spinal cord slice, central nervous system, peripheral nervous system, or nerve.

In certain embodiments, the brain structure is the striatum, basal ganglia, nucleus accumbens, or their anatomical and/or functional counterparts in other mammalian species.

In certain embodiments, the cell or tissue is a human cell or human tissue.

In certain embodiments, the cell or tissue is a cell.

In certain embodiments, the cell or tissue is a tissue.

In certain embodiments, the cell or tissue is a whole animal.

In certain embodiments, the cell or tissue is a human.

According to the invention, treatment of a subject in vivo with a potential agent for use as an anti-psychotic drug preferably produces a distinct phosphorylation pattern of intracellular signaling proteins: DARPP-32 at two sites (Thr34 and Thr75), ERK1 at two sites (Thr202 and Tyr204), ERK2 at two sites (Thr185 and Tyr187), and CREB at one site (Ser133).

For example, a typical anti-psychotic, e.g., haloperidol (e.g., at a dosage of 0.2 mg/kg), or a selective dopamine D2 receptor antagonist, e.g., eticlopride (e.g., at a dosage of 0.5 mg/kg), preferably will produce significant increases in the levels of phospho-ERK1 (i.e. phospho-Thr202 and phospho-Tyr204) and phospho-ERK2 (i.e. phospho-Thr185 and phospho-Tyr187), as well as phospho-CREB (i.e., phospho-Ser133). In certain embodiments, protein phosphorylation will be maximally increased about 15 minutes following administration of the potential agent. Phospho-ERK2 levels will return to control levels 30 minutes after administration of the typical anti-psychotic, e.g., haloperidol. Phospho-CREB levels will return to control levels 30 minutes after typical anti-psychotic (e.g., haloperidol) administration. Phospho-ERK1 levels will still be significantly higher than control values at 60 minutes.

In contrast, treatment with an atypical anti-psychotic, e.g., clozapine (e.g., at a dosage of 5.0 mg/kg), preferably will produce a rapid decrease in the levels of phospho-ERK2 and phospho-CREB at 15, 30 and 60 minutes. Phospho-ERK1 levels will be decreased at 60 minutes after administration of the atypical anti-psychotic.

In the case of DARPP-32 phosphorylation, all three categories of drugs (typical anti-psychotic, atypical anti-psychotic and selective dopamine D2 receptor antagonist) preferably will increase phosphorylation at Thr34 site of DARPP-32. With administration of a typical anti-psychotic such as haloperidol, Thr 34 phosphorylation will increase for up to 30 minutes, but at 60 minutes, there will be no statistical difference from controls. However, in the case of phosphorylation at the Thr-75 site of DARPP-32, preferably only treatment with an atypical anti-psychotic, e.g., clozapine, will significantly increase phosphorylation levels of DARPP-32 at 15, 30 and 60 minutes. A selective dopamine D2 receptor antagonist, e.g. eticlopride, preferably will decrease DARPP-32 phosphorylation at Thr75 of DARPP-32 30 minutes after administration, while a typical anti-psychotic e.g., haloperidol, preferably will be without effect.

In one embodiment, experimental animals (preferably mice) are administered a potential agent, e.g., by intraperitoneal injection. Animals are sacrificed by decapitation post-injection, e.g., at 15, 30, or 60 minutes post-injection. After decapitation, heads are immediately immersed in liquid nitrogen for a time sufficient to inactivate all protein activity. Brains are then dissected (preferably under conditions that prevent or minimize thawing) and a portion of the brain of interest, e.g., the striatum, is then removed, homogenized by standard methods, preferably by sonication, in an appropriate, art-known medium, e.g., 1% SDS, and then preferably boiled. Levels of phosphorylated DARPP-32, CREB, and ERK1 and ERK2 are then determined according to the methods disclosed herein.

In another embodiment, cultured cells, e.g., cultured striatal neurons, are contacted with a potential agent, the cells are then homogenized and levels of phosphorylated DARPP-32, CREB, and ERK1 and ERK2 are then determined according to the methods disclosed herein.

In order to determine levels of phosphoproteins in a cell or tissue, e.g. brain tissue or cultured neuronal cells, aliquots of brain homogenate or of homogenates of cultured cells, may be separated by SDS/PAGE analysis according to standard methods, e.g., SDS/PAGE analysis using 10% polyacrylamide gels. The separated proteins may be analyzed by any method known in the art. In one embodiment, proteins are analyzed by immunoblot analysis. In certain embodiments, the proteins are transferred, after separation to poly(vinylidene difluoride) membranes as described by Towbin and colleagues (Towbin, H. et al. 1979. *Proc. Natl. Acad. Sci. USA* 76:4350-4354), for further analysis.

The effect of the agent on the phosphorylation of DARPP-32 at either of two sites (Thr34 and/or Thr75), ERK1 at either of two sites (Thr202 and/or Tyr204), ERK2 at either of two sites (Thr185 and/or Tyr187) and/or CREB at one site (Ser133) can be assessed using, e.g., phosphorylation state-specific antibodies according to standard methods.

In certain embodiments, DARPP-32 is human DARPP-32.

In certain embodiments of the above-described methods for identifying agents as a potential atypical or typical anti-psychotic compound, CREB is human CREB.

In certain embodiments of the above-described methods for identifying agents as a potential atypical or typical anti-psychotic compound, ERK1 is human ERK1.

In certain embodiments of the above-described methods for identifying agents as a potential atypical or typical anti-psychotic compound, ERK2 is human ERK2.

In certain embodiments of the above-described methods for identifying agents as a potential atypical or typical anti-psychotic compound, DARPP-32 is mouse DARPP-32.

In certain embodiments of the above-described methods for identifying agents as a potential atypical or typical anti-psychotic compound, CREB is mouse CREB.

In certain embodiments of the above-described methods for identifying agents as a potential atypical or typical anti-psychotic compound, ERK1 is mouse ERK1.

In certain embodiments of the above-described methods for identifying agents as a potential atypical or typical anti-psychotic compound, ERK2 is mouse ERK2.

In another embodiment, the present invention provides a method of identifying compounds capable of producing atypical anti-psychotic activity in vitro or in vivo. The method is based on the determination of patterns of levels of DARPP-32, ERK1, ERK2 and CREB phosphorylation both before and after treatment of cells or tissues with a test compound. The in vitro and in vivo applications would include, but not be limited to, treatment with a test compound of whole animals, in tissue slices, in broken cell preparations, in intact cells (including cell lines and primary cultures), and in isolated and purified cell preparations. As a result, the present invention also includes compositions identified by this method. One of skill would understand that once identified as capable of producing altered DARPP-32, ERK1, ERK2 and CREB phosphorylation level patterns similar to known atypical antipsychotic compounds, the compound could be used to treat an anti-psychotic disorder. Such a disorder would include, but not be limited to, psychotic depression, postpartum depression, affective disorder, schizoaffective disorder, schizophreniform disorder, schizophrenia, delusional disorder, brief psychotic disorder, shared psychotic disorder, borderline personality disorder, manic-depressive disorder, obsessive-compulsive disorder, Huntington's Disease, Tourette's syndrome and tic disorder. In the context of the present invention, the compounds identified would be administered as an effective dose or amount, which can be determined by one of skill in the art based on data from studies such as presented in this specification. Such data would include, but not be limited to, results from IC50 determinations.

As would be clearly understood by a person of ordinary skill in the art, any and/or all of the embodiments disclosed herein for identifying an agent, drug or compound that can produce altered DARPP-32, ERK1, ERK2 and CREB phosphorylation level patterns similar to known atypical anti-psychotic compounds, including such procedures that incorporate rational drug design, as disclosed herein, can be combined to form additional drug screens and assays, all of which are contemplated by the present invention.

In other embodiments, the agent may be co-administered along with a known atypical anti-psychotic compound, e.g., clozapine, risperidone, iloperidone, olanzapine, quetiapine zotepine, perospirone and ziprasidone. The amount (and/or rate) of modulation of DARPP-32, ERK1, ERK2 and CREB phosphorylation is then determined. Since the administration of an atypical anti-psychotic compound in the absence of the agent should result in an increase in phosphorylation of Thr34-DARPP-32 and Thr75-DARPP-32, and a decrease in phosphorylation of phospho-Thr202 ERK1, phospho-Tyr204 ERK1, phospho-Thr185 ERK2, phospho-Tyr187 ERK2, and phospho-Ser133 CREB, an agent is identified as capable of modulating DARPP-32, ERK1, ERK2 and CREB phosphorylation when the amount (and/or rate) of phosphorylation is significantly increased or decreased in the presence of the agent relative to in the absence of the agent.

The in vivo method can further comprise administering the agent to a non-human mammal. In certain preferred embodiments, the non-human mammal is a wild-type non-human mammal. In other embodiments, the non-human mammal may be an animal model for a disease or disorder.

In a specific embodiment, the animal model is a homozygous DARPP-32 knockout mouse (see U.S. Pat. No.: 5,777, 195, by Fienberg et al., issued Jul. 7, 1998; U.S. Pat. No.6, 013,621, by Nishi et al., issued Jan. 11, 2000; and Fienberg et al.,1998, Science 281:838-842; each of which is incorporated herein by reference in its entirety). In one embodiment, the homozygous DARPP-32 knockout mouse may be used, in an additional test or assay, to validate or confirm that a candidate agent modulates Thr34- and Thr75 DARPP32 phosphorylation. In one embodiment, the knockout mouse is administered a candidate anti-psychotic agent, and the agent's effects on the mouse's behavior are analyzed, to confirm that the effect seen upon administration of the agent to a wild-type mouse is not seen in the knockout mouse. In a specific embodiment, the validation may be carried out according to the methods described in Nishi et al. (U.S. Pat. No. 6,013,621, issued Jan. 11, 2000). When such an agent is identified that modulates Thr34- and Thr75 DARPP32 phosphorylation, the presence of or administration of the agent in the DARPP-32 knockout mouse should not significantly increase or decrease the amount (and/or rate) of phosphorylation dependent activation of AMPA receptors relative to the absence or non-administration of the agent.

In certain embodiments, combinatorial libraries of chemical compounds, based on different structural skeletons (e.g., purines), as well as unrelated naturally occurring compounds, can be tested as drug candidates. In a preferred embodiment of this type, the assay is performed using high throughput technology with automated robotic technology as disclosed herein. Positive results ("hits") represent an increase in phosphorylation of Thr34-DARPP-32 and Thr75-DARPP-32, and a decrease in phosphorylation of phospho-Thr202 ERK1, phospho-Tyr204 ERK1, phospho-Thr185 ERK2, phospho-Tyr187 ERK2, and phospho-Ser133 CREB, as compared to the control reactions (in which the drug candidate is not included in the assay).

In certain embodiments, the invention provides a computer system for identifying an agent to be tested for an ability to treat a psychotic disorder in a patient in need of such treatment, the computer system comprising a processor, and a memory encoding one or more programs coupled to the processor, wherein the one or more programs cause the processor to perform any one of the methods any one of the methods described herein for identifying agents as a potential atypical or typical anti-psychotic compound. In certain embodiments, the computer system comprises a database that includes a plurality of records containing information relating to phosphorylation patterns observed for particular potential compounds of interest. Such relational databases are well known in the art.

Once a drug candidate is selected, structural variants of the drug candidate can be tested. These compounds can also be scrutinized and modified with parameters such as membrane permeability, specificity of effects, and toxicity. The selected (e.g., the most potent) compounds of this secondary screening can then be evaluated in situ and in animal models (see Section 4.3) to determine whether the selected compounds increase phosphorylation of Thr34-DARPP-32 and Thr75-DARPP-32, and decrease phosphorylation of phospho-Thr202 ERK1, phospho-Tyr204 ERK1, phospho-Thr185 ERK2, phospho-Tyr187 ERK2, and phospho-Ser133 CREB, and/or induce predicted behavioral alterations with minimal to no side-effects. Such behavioral abnormalities may include, but not be limited to, testing locomotor activity, e.g., administration of a drug candidate to mice and observation of increased or decreased locomotor activity (see, e.g., Kosten et al., J. Pharmacol., Exp. Ther. 269:137-144 (1994); U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety); and/or self-administration of selected drugs or in prepulse inhibition (see, e.g., U.S. Pat. No. 5,777,195 Issued Jul. 7, 1998, incorporated herein by reference in its entirety). These tests can then be followed by human trials in clinical studies. Alternatively, in certain embodiments, human trials in clinical studies can be performed without animal testing.

Alternatively, modulators of phosphorylation of Thr34-DARPP-32 and Thr75-DARPP-32, phospho-Thr202 ERK1, phospho-Tyr204 ERK1, phospho-Thr185 ERK2, phospho-Tyr187 ERK2, and phospho-Ser133 CREB, can be obtained by screening, e.g., a random peptide library produced by recombinant bacteriophage (see, e.g., Scott and Smith, Science 249:386-390 (1990); Cwirla et al., Proc. Natl. Acad. Sci. USA 87:6378-6382 (1990); Devlin et al., Science 249:404-406 (1990)) or a chemical library. Using the "phage method" very large libraries can be constructed (106-108 chemical entities). A second approach may be to use chemical methods, of which the Geysen method (Geysen et al., Molecular Immunology 23:709-715 (1986); Geysen et al. J. Immunologic Method 102:259-274 (1987)) and the method of Fodor et al. (Science 251:767-773 (1991)) are examples. Furka et al. (14th international Congress of Biochemistry, Volume 5, Abstract FR:013 (1988); Furka, Int. J. Peptide Protein Res. 37:487-493 (1991)), Houghton (U.S. Pat. No. 4,631,211, issued December 1986) and Rutter et al. (U.S. Pat. No. 5,010, 175, issued Apr. 23, 1991) disclose methods to produce a mixture of peptides that can be tested as modulators of, e.g., CK1, Cdk5, AMPA receptor, PKA, PKG, PP-1, PP2C, PP2B and/or PP2A activity.

In another aspect, synthetic libraries (Needels et al., Proc. Natl. Acad. Sci. USA 90:10700-4 (1993); Ohlmeyer et al., Proc. Natl. Acad. Sci. USA 90:10922-10926 (1993); Lam et al., International Patent Publication No. WO 92/00252; Kocis et al., International Patent Publication No. WO 94/28028, each of which is incorporated herein by reference in its entirety), and the like can be used to screen for modulators of phosphorylation of Thr34-DARPP-32 and Thr75-DARPP-32, phospho-Thr202 ERK1, phospho-Tyr204 ERK1, phospho-Thr185 ERK2, phospho-Tyr187 ERK2, and phospho-Ser133 CREB, according to the present invention. Once a potential modulator is identified, chemical analogues can be either selected from a library of chemicals as are commercially available (e.g., from Chembridge Corporation, San Diego, Calif. or Evotec OAI, Abingdon, UK), or alternatively synthesized de novo. The prospective agent (drug) can be placed into any standard assay to test its effect on phosphorylation of Thr34-DARPP-32 and Thr75-DARPP-32, phospho-Thr202 ERK1, phospho-Tyr204 ERK1, phospho-Thr185 ERK2, phospho-Tyr187 ERK2, and phospho-Ser133 CREB. A drug is then selected as an atypical anti-psychotic that increases phosphorylation of Thr34-DARPP-32 and Thr75-DARPP-32, and decreases phosphorylation of phospho-Thr202 ERK1, phospho-Tyr204 ERK1, phospho-Thr185 ERK2, phospho-Tyr187 ERK2, and phospho-Ser133 CREB.

The present invention also contemplates screens for small molecules, analogs thereof, as well as screens for natural modulators of phosphorylation of Thr34-DARPP-32 and Thr75-DARPP-32, phospho-Thr202 ERK1, phospho-Tyr204 ERK1, phospho-Thr185 ERK2, phospho-Tyr187 ERK2, and phospho-Ser133 CREB, such as those molecules that bind to and inhibit or activate DARPP-32, ERK1, ERK2, and CREB in vivo. Alternatively, natural products libraries can be screened using assays of the invention for molecules that modulate DARPP-32, ERK1, ERK2, and CREB phosphorylation.

In one particular assay, the target e.g., DARPP-32, ERK1, ERK2, and CREB, can be attached to a solid support. Methods for placing such targets on the solid support are well known in the art and include such things as linking biotin to the target and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the target can be determined. Alternatively, or in addition, the dissociation constant between the labeled potential modulator and the target, for example, can be determined. Suitable labels for either the target or the potential modulator are disclosed herein.

In another embodiment, an animal model, as disclosed hereinbelow, can be used to ascertain the effect of a potential agent on a psychotic condition. A potential modulator that ameliorates the psychotic condition can then be selected. For example, a locomotor behavioral response of the animal can be determined in the presence and absence of the agent. In specific embodiment, locomotor activity of an animal, e.g., a mouse can be measured in an activity monitor.

Methods of testing a potential therapeutic agent (e.g., a candidate drug, potential modulator, etc.) in an animal model are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined. Animals can be sacrificed by decapitation, focused microwave beam irradiation, or other standard methods.

In one embodiment, an animal disease model is employed to assess the potential efficacy of these compounds in relieving pathological symptoms of psychosis. For example, animals ectopically expressing the human disease causing form of the Huntington s disease (HD) gene exhibit neuropathological symptoms similar to those of HD patients. Models such as these can be used to assess the efficacy of any potential therapeutic agents (see Section 4.3). Generally, at least two groups of animals are used in the assay, with at least one group being a control group in which the administration vehicle is administered without the potential modulator.

4.1.1. Phosphorylation Assays

In certain embodiments of the above-described methods for identifying agents as a potential atypical or typical antipsychotic compound, the level of phosphorylation or dephosphorylation is detected with a phosphospecific antibody. Phosphorylation of a peptide substrate can be detected via direct binding of phosphorylation state-specific ("phosphospecific") antibodies or by measuring displacement of a phosphospecific antibody from a competitor phosphopeptide (see, e.g., Parker, Law et al., 2000, Development of high throughput screening assays using fluorescence polarization: nuclear receptor-ligand-binding and kinase/phosphatase assays, J. Biomolec. Screening 5(2): 77-88). Phosphorylated peptides may also be detected using the methods of Bader et al. (2001, A cGMP-dependent protein kinase assay for high throughput screening based on time-resolved fluorescence resonance energy transfer, Journal of Biomolecular Screening 6(4): 255-64).

Methods of producing phosphospecific antibodies are well known in the art. In one embodiment, the methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, (each of which is incorporated herein by reference in its entirety) are used to produce phosphorylation state-specific antibodies having specificity for Thr34-phosphorylated and Thr75-phosphorylated DARPP-32.

Phosphorylation state-specific antibodies against phosphoserine, phosphothreonine, or phosphotyrosine are commercially available. These antibodies are useful for determining whether proteins are phosphorylated in general, and on which residue. Such antibodies are available from commercial sources (see, e.g., Smith, The Scientist 15[4]:24, Feb. 19, 2001 for list of commercial sources, including Santa Cruz Biotechnology Inc., Sigma RBI, Stratagene, Upstate Biotechnology and Zymed).

Fluorescence methods such as fluorescence resonance energy transfer (FRET) or fluorescence polarization (FP) (see, e.g., Parker, Law et al., 2000, Development of high throughput screening assays using fluorescence polarization: nuclear receptor-ligand-binding and kinase/phosphatase assays, J. Biomolec. Screening 5(2): 77-88) can be used to detect the specific phosphopeptide-antibody complexes. These methods have the advantage that they employ "homogeneous" detection that is not dependent on isolation of the bound species, but rather depends on changes in fluorescence that occur owing to specific binding in solution.

Fluorescence resonance energy transfer, or FRET, is widely used for homogeneous assays capable of detecting specific binding of macromolecules. FRET depends on the ability of excited "donor" fluorescent molecules (fluorophores) to transfer their energy to nearby "acceptor" fluorophores rather than emitting light. Thus, when the two fluorophores are brought together in space by binding to a substrate target, fluorescence emitted at the normal donor wavelength is reduced and fluorescence emitted by the acceptor fluorophore increases. Either the decrease in donor fluorescence or the increase in acceptor fluorescence can be used to measure the binding event.

Pairs of fluorophores, such as coumarin and fluorescein isothiocyanate, can be used. Pairs of such molecules that can engage in fluorescence resonance energy transfer (FRET) are termed FRET pairs. In order for energy transfer to occur, the donor and acceptor molecules must typically be in close proximity (up to 70 to 100 Å (Clegg, 1992, Methods Enzymol. 211:353-388; Selvin, 1995, Methods Enzymol. 246: 300-334). The efficiency of energy transfer falls off rapidly with the distance between the donor and acceptor molecules. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Fluorescence polarization measurements can also be used for measuring the phosphorylation state of a peptide or protein (see, e.g., Parker, Law et al., 2000, Development of high throughput screening assays using fluorescence polarization: nuclear receptor-ligand-binding and kinase/phosphatase assays, J. Biomolec. Screening 5(2): 77-88; Turek et al., 2001, Anal. Biochem. 299: 45-53). Binding of a large specific antibody to a fluorescent small phosphopeptide slows its tumbling rate and increases the fluorescence polarization signal. Thus fluorescence polarization is proportional to the amount of bound fluorescent phosphopeptide. This assay can be used in a competitive mode, in which a fixed concentration of fluorescent peptide and antibody are added to a biological sample, and the presence of non-fluorescent phosphoprotein or phosphopeptide is recorded as a decrease in signal. It can also be used in a direct binding mode, in which phosphate addition (by kinase) or removal (by phosphatase) modulates antibody binding and thus polarization signal. In a specific embodiment, a fluorescence polarization assay is performed using the methods of Turek et al. (2001, Anal. Biochem. 299: 45-53), in which a product-specific anti-phosphorylated peptide-specific (e.g., anti-phospho-scrine) antibody is used.

4.1.2. Enzymatic Assays for Kinases and Phosphatases

In certain embodiments of the invention, a modulation in the phosphorylation pattern of DARPP-32, ERK1, ERK2, and/or CREB may be also assayed by monitoring modulation of activity of the kinases that phosphorylate DARPP-32, ERK1, ERK2, and/or CREB, and/or phosphatases that dephosphorylate DARPP-32, ERK1, ERK2, and/or CREB. In certain embodiments, modulation of activity of CdkS (which phosphorylates Thr75), PKA (which phosphorylates Thr34 and Ser133 CREB), and/or p90 ribosomal S6 kinase ("p90RSK," which phosphorylates ERK1 and ERK2) is monitored.

Kinase activities can be monitored by a variety of methods known to those skilled in the art, e.g., the methods disclosed in Parker, Law, et al., 2000, Development of high throughput screening assays using fluorescence polarization: nuclear receptor-ligand-binding and kinase/phosphatase assays, J. Biomolec. Screening 5(2): 77-88; Bader et al. (2001, Journal of Biomolecular Screening 6(4): 255-64); Liu, F., X. H. Ma, et al. (2001). "Regulation of cyclin-dependent kinase 5 and casein kinase 1 by metabotropic glutamate receptors." Proceedings of the National Academy of Sciences of the United States of America 98(20): 11062-8; Evans, D. B., K. B. Rank, et al. (2002). "A scintillation proximity assay for studying inhibitors of human tau protein kinase II/Cdk5 using a 96-well format." Journal of Biochemical & Biophysical Methods 50(2-3): 151-61.

Using such methods, samples containing the kinase of interest are exposed under the appropriate conditions to radioactive ATP and a synthetic peptide substrate of the appropriate composition to provide a site for phosphorylation. The radioactive phosphate newly associated with the peptide is then measured. Addition of a chemical moiety, such as biotin covalently linked to the substrate peptide, allows binding of the substrate peptide by a streptavidin-coated bead. Bead-bound peptide can be isolated and associated radioactivity measured, or, preferably, radioactivity associated with the substrate peptide can be measured directly using a bead suitable for scintillation proximity assays.

Activities of protein phosphatases can be monitored by a variety of methods known to those skilled in the art, e.g., the methods disclosed in Cohen et al. (1988, Protein phosphatase-1 and protein phosphatase-2A from rabbit skeletal muscle, Methods Enzymol 159:390-408) or Stewart and Cohen (1988, Protein phosphatase-2B from rabbit skeletal muscle: a $Ca^{2+}$-dependent, calmodulin-stimulated enzyme, Methods Enzymol 159:409-16).

DARPP-32 phosphorylation, i.e., Ser137 DARPP-32 phosphorylation (CK1), Thr75 DARPP-32 phosphorylation (Cdk5) or Thr34 DARPP-32 phosphorylation (PKA, PP2B, PP1) may also be measured according to methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000; and in U.S. Pat. No. 5,777,195, by Fienberg et al., issued Jul. 7, 1998, each of which is incorporated herein by reference in its entirety.

In certain embodiments, modulators (e.g., inhibitors) of Cdk5 can be identified via enzymatic assays using recombinant Cdk5 purified from bacteria after expression using vectors, using cell lysates containing Cdk5, or using brain tissue lysates (see, e.g., Leost et al., 2000, Eur. J. Biochem. 267: 5983-5994). In other embodiments, modulators of Cdk5 can be identified via enzymatic assays using recombinant Cdk5 purified from insect cells (e.g., Sf9 cells) after expression using baculovirus. In such assays, an enzyme or lysate is incubated at 30° C. with peptide substrate biotin-DARPP-32 (amino acid residues 67-82) (approximately 1 μM), in an appropriate buffer (500 μM ATP, 50 mM HEPES, pH7.5/10 mM $MgCl_2$, 1 mM dithiothreitol), in a final reaction volume of 40-60 μl. The reaction is halted by addition of an equal volume of stop buffer (30 mM EDTA, pH 7.0).

For detection of phosphorylated peptide, aliquots of the stopped reaction (20-30 μl) are added in triplicate to a 384-well black multiwell plate, followed by addition of two volumes of antibody mix containing rabbit polyclonal anti-phosphothr75-DARPP-32 antibody (1 nM), europium-labeled anti-rabbit IgG (1 nM), and streptavidin-allophycocyanin conjugate (2 μg/ml), in an appropriate buffer (0.1% BSA in phosphate-buffered saline, pH 7.4). After incubation at 20° C. for 1-24 hr, fluorescence is measured (excitation filter wavelength 340 nM; emission filter wavelength 660 nM) over a 200-μs period starting 50 μs after the excitation using Applied Biosystems Cytofluor. Other antibody combinations, such as a mouse monoclonal anti-phosphothr75 DARPP-32 and europium-labeled anti-mouse IgG, are contemplated according to the invention, and would be expected to give comparable results.

In one form of the above-disclosed assay, recombinant enzyme, enzyme isolated from tissue, or tissue or cell lysate is incubated at 30° C. with biotin-peptide substrate providing a proline-directed phosphorylation site. Amino acid residues 67-82 of human DARPP-32, KRPNPCAYTPPSLKAV (SEQ ID NO: 5), which are identical to phosphorylation sites in rat and mouse DARPP-32, provide such a substrate.

In another embodiment, a cell-based assay for phosphorylation is used. In a specific embodiment, signal transduction based on protein phosphorylation is visualized in vivo, e.g., in single living cells using fluorescent indicators, using methods such as those disclosed in Sato et al. (2002, Fluorescent indicators for imaging protein phosphorylation in single living cells, Nature Biotechnology 20(3): 287-94). Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

4.2. Compounds that Modulate the Phosphorylation Patterns of DARPP-32, ERK1, ERK2 and CREB The present invention also encompasses methods for designing new chemical compounds that have activity as modulators of DARPP-32, ERK1, ERK2 and CREB phosphorylation, wherein these new chemical compounds may include, but not be limited to, any compound with the ability to either stimulate or inhibit DARPP-32, ERK1, ERK2 and CREB phosphorylation, and would include, but not be limited to, low molecular weight organic molecules capable of being delivered intracellularly.

The present invention further provides a method of performing rational drug design to develop drugs that can modulate DARPP-32, ERK1, ERK2 and CREB phosphorylation and thereby ameliorate a psychotic disorder. Such rational drug design can be performed using compounds that have been identified as agonists or antagonists of DARPP-32, ERK1, ERK2 or CREB phosphorylation as a starting point. Thus, the present invention provides screens and assays to allow more specific modulators to be identified. Such methods of rational drug design are well-known in the art. In a specific embodiment, the rational drug design methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties, are used.

Indeed, potential modulators can be examined through the use of computer modeling using a docking program such as GRAM, DOCK, or AUTODOCK (Dunbrack et al., Folding & Design 2:27-42 (1997)), to identify potential modulators of, e.g., DARPP-32, ERK1, ERK2 or CREB phosphorylation. These modulators can then be tested for their effect on DARPP-32, ERK1, ERK2 or CREB phosphorylation.

Preferably the candidate atypical antipsychotic agent, compound or composition identified by the methods of screening disclosed herein can cross through the blood brain barrier in sufficient quantities and at a sufficient rate so as to allow the treatment of a psychotic disorder. In one such embodiment, the agent is administered intravenously. In another embodiment, the agent is administered orally. More preferably the agent can cross the blood brain carrier without a carrier (for methods and routes of administration, see Section 4.4).

The invention also encompasses pharmaceutical compositions for regulating DARPP-32, ERK1, ERK2 or CREB phosphorylation, and/or treating a psychotic disorder. Because a loss of normal function results in the development of a phenotype of the above-listed diseases or disorders, increased phosphorylation of Thr34 DARPP-32 and/or Thr75 DARPP-32, and decreased phosphorylation of Thr202 and/or Tyr204 ERK1, Thr185 and/or Tyr187 ERK2 and/or Ser133-CREB, facilitates amelioration of a symptom in individuals exhibiting a symptom of such a disorder.

4.3. Animal Models

According to the methods of the invention, an animal model for a psychotic disease or disorder, including but not limited to psychotic depression, postpartum depression, affective disorder, schizoaffective disorder, schizophreniform disorder, schizophrenia, delusional disorder, brief psychotic disorder, shared psychotic disorder, borderline personality disorder, manic-depressive disorder, obsessive-compulsive disorder, Huntington's Disease, Tourette's syndrome and tic disorder, may be used in assays to screen for compounds that modulate the activity of DARPP-32, ERK1, ERK2 and CREB, or for compounds that ameliorate the symptoms of a psychotic disorder.

In one embodiment, an animal model for psychotic disorder is used in screening assays according to the methods of the invention. Such animals can be mice, rats, hamsters, sheep, pigs, cattle, etc., and are preferably non-human mammals.

In one embodiment, a mouse model of schizophrenia is used (Sipes et al., 1995, 8-OH-DPAT disruption of prepulse inhibition in rats: reversal with (+)WAY 100,135 and localization of site of action, Psychopharmacology (Berl) 117(1): 41-8; Cao et al., 2002, Brain Research 937: 32-40). Such a model animal system may be used to screen for compounds useful in the treatment of schizophrenia.

In another embodiment, a mouse model of Parkinson's disease is used (Uhl et al., 1985, Lancet 1:956-57; Mokry, 1995, Experimental models and behavioral tests used in the study of Parkinson's Disease, Physiol. Res. 44: 143-50.; Du, 2001, Proc. Natl. Acad. Sci. USA 98: 14669-14674). Such a model animal system may be used to screen for compounds useful in the treatment of Parkinson's disease due to their effect on 5-HTR intracellular signaling pathways. In an alternative embodiment, a rat model of Parkinson's disease is used. In a specific embodiment, rats are unilaterally (i.e. in one hemisphere) injected with 6-OHDA (6-hydroxydopamine; a dopaminergic neurotoxin) according to standard methods. The 6-OHDA is selectively taken up by dopaminergic neurons and kills the neurons. Such 6-OHDA-lesioned animals are considered an animal model of Parkinson's disease.

In a specific embodiment, the animal model is a homozygous DARPP-32 knockout mouse (see U.S. Pat. No. 5,777, 195, by Fienberg et al., issued Jul. 7, 1998; U.S. Pat. No. 6,013,621, by Nishi et al., issued Jan. 11, 2000; and Fienberg et al., 1998, Science 281:838-842; each of which is incorporated herein by reference in its entirety). In one embodiment, the homozygous DARPP-32 knockout mouse may be used, in an additional test or assay to validate or confirm that a candidate agent modulates DARPP-32 phosphorylation. In a specific embodiment, the validation may be carried out according to the methods described in Nishi et al. (U.S. Pat. No. 6,013,621, issued Jan. 11, 2000). When such an agent is identified that modulates the activity of DARPP-32 phosphorylation, the presence of or administration of the agent in the DARPP-32 knockout mouse should not significantly increase or decrease the amount (and/or rate) of activation of ligand-operated and/or voltage-operated ion channels, relative to the absence or non-administration of the agent, as would be apparent to one of skill in the art.

4.4. Pharmaceutical Formulations

The present invention provides pharmaceutical compositions of the agents, drugs or compounds of the invention disclosed hereinabove. The agent, drug or compound, or their physiologically acceptable salts or solvates, may be formulated for administration for injection, or for oral, topical, nasal, inhalation, insufflation (either through the mouth or the nose) buccal, parenteral, rectal administration or other forms of administration. The invention provides pharmaceutical compositions comprising effective amounts of an agent(s) of the invention together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, etc. or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one, which is disclosed in U.S. Pat. No. 4,052,988), alkyl substituted derivatives of p-dioxanone (i.e., 6,6-dimethyl-1,4-dioxan-2-one which is disclosed in U.S. Pat. No. 5,703,200), triethylene carbonate (1,3-dioxan-2-one), alkyl substituted derivatives of 1,3-dioxanone (which are disclosed in U.S. Pat. No. 5,412,068), delta-valerolactone, beta-butyrolactone, gamma-butyrolactone, epsilon-decala tone, hydroxybutyrate, hydroxyvalerate, 1,4-dioxepan-2-one (disclosed in U.S. Pat. No. 4,052,988 and its dimer 1,5,8,12-tetraoxacyclotetradecane-7,14 dione), 1,5-dioxepan-2-one, and polymer blends thereof.

Such compositions may influence physical state, stability, rate of in vivo release, and rate of in vivo clearance of the present proteins and derivatives. See, e.g., Remington s Pharmaceutical Sciences, 18th ed., (1990, Mack Publishing Co., Easton, Pa. 18042) pages 1435-1712). The compositions may be prepared in liquid form, or be in dried powder, such as lyophilized form.

Contemplated for use herein are oral solid dosage forms, which are disclosed generally in Remington s Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported U.S. Pat. No. 4,925,673). Liposomal encapsulation may be used and the lipomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979). In general, the formulation will include the agent and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L3OD, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, a-lactose, anhydrous lactose, cellulose (e.g., microcrystalline cellulose), sucrose, calcium hydrogen phosphate modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent stiCK1ng during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present n the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane, which allows water to enter and to push the drug out through a single small opening due to osmotic effects.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g.,gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

4.4.1. Dosage Determinations

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

4.4.2. Routes of Administration

The component or components of a therapeutic composition of the invention may be introduced parenterally, topically, or transmucosally, e.g., orally, nasally, or rectally, or transdermally. Preferably, administration is parenteral, e.g., via intravenous injection, and also including, but not limited to, intra-arteriole, intramuscular, intradermal, subcutaneous, intraperitoneal, intraventricular, and intracranial administration. In preferred embodiments, the component or components of a therapeutic composition of the invention is introduced orally or parentally.

In preferred embodiments of the invention, an agent (or drug or compound) can cross and more preferably readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc.

In another embodiment, an agent of the present invention is administered via the standard procedure of drilling a small hole in the skull to administer the agent.

In another embodiment, the molecule can be administered intracranially or, more preferably, intraventricularly. In another embodiment, osmotic disruption of the blood-brain barrier can be used to effect delivery of agent to the brain (Nilaver et al., Proc. Natl. Acad. Sci. USA 92:9829-9833 (1995)). In yet another embodiment, an agent can be administered in a liposome targeted to the blood-brain barrier. Administration of pharmaceutical agents in liposomes is known (see Langer, Science 249:1527-1533 (1990); Treat et al., in Liposomes in the Therapy of infectious Disease and Cancer, Lopez-Berestein and Fidler (eds.), Liss, New York, pp. pp. 317-327 and 353-365 (1989). All of such methods are envisioned in the present invention.

Although some predictions have been made concerning the ability of molecules to pass through the blood-brain barrier, these predictions are at best speculative. The rate and extent of entry of a compound into the brain are generally considered to be determined by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, J. Pharm. Sci. 61:589 (1972); Hansch et al., J. Pharm. Sci. 76:663 (1987)). In practice, the octanol-water partition system only provides a qualitative indication of the capability of a compound to cross the blood-brain barrier. For example, comparisons between known histamine H2 receptor antagonists suggest that there is no such simple relationship between their brain penetration and octanol water partition coefficients (Young et al., J. Med. Chem. 31:656 (1988)). Other factors, besides the octanol-water partition influence the propensity to cross the blood-brain barrier. Comparison of the ability of histamine H2 receptor antagonists to cross the blood-brain barrier suggests that brain penetration may increase with decreasing over-all hydrogen binding ability of a compound (Young et al., J. Med. Chem. 31:656 (1988)). Begley et al. (J. Neurochem. 55:1221-1230 (1990)) herein incorporated by reference in its entirety, discloses the ability of cyclosporin A to cross the blood-brain barrier. Methodology as used by Begley et al. includes: (1) measuring the brain uptake index (BUI) with the equation for a tritiated agent compound:

BUI=[(brain $^3$H/brain $^{14}$C)/(injectate $^3$H/injectate $^{14}$C)]× 100 where the $^{14}$C reference compound is $^{14}$C butanol or an analogous solvent; (2) Brain perfusion studies; (3) Intravenous bolus injection studies; and (4) Studies with cultured cerebral capillary endothelium.

In another embodiment, the therapeutic compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 317-327 and 353-365 (1989)). To reduce its systemic side effects, this may be a preferred method for introducing the agent.

In another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The following experimental example is offered by way of illustration and not by way of limitation.

5. EXAMPLE 1

In Vivo Treatment with Haloperidol, Clozapine or Eticlopride Produces Distinct Phosphorylation Patterns of DARPP-32, CREB, AND ERK1 and ERK2

This example demonstrates that in vivo treatment with haloperidol, clozapine or eticlopride produces distinct phosphorylation patterns of DARPP-32, CREB, ERK1 and ERK2. These data demonstrate that typical and atypical anti-psychotics can be differentiated or discriminated based on phosphorylation patterns of intracellular signaling proteins. The data indicate that candidate drugs can be screened on the basis of differential phosphorylation patterns of DARPP-32, CREB, ERK1 and ERK2 to classify their activity as typical or atypical anti-psychotics, and then to identify appropriate candidates for further testing and development.

5.1. Materials and Methods

Male C57/BL6 mice (groups of six) were administered intraperitoneal injections of one of three anti-psychotic compounds, haloperidol (a typical anti-psychotic), clozapine (an atypical anti-psychotic), or eticlopride (a selective dopamine D2 receptor antagonist). All animals were sacrificed by decapitation at 15, 30, or 60 minutes post-injection. After decapitation, the heads were immediately immersed in liquid nitrogen for 6 seconds to inactivate all protein activity. The brains were then dissected on an ice-cold surface and the striata removed and sonicated in 750 μl of 1% SDS, and then boiled for 10 minutes. Levels of phosphorylated DARPP-32, CREB, and ERK1 and ERK2 were then determined.

In order to determine levels of phosphoproteins in brain tissue, aliquots of the brain homogenate were loaded onto 10% polyacrylamide gels and the proteins separated by SDS/PAGE analysis, and then transferred to poly(vinylidene difluoride) membranes as described by Towbin and colleagues (Towbin, H. et al. 1979. *Proc. Natl. Acad. Sci. USA* 76:4350-4354). The effect of the drugs on the phosphorylation of DARPP-32 at two sites (Thr34 and Thr75), ERK1 at two sites (Thr202 and Tyr204), ERK2 at two sites (Thr185 and Tyr187), and CREB at one site (Ser133) was assessed using phosphorylation state-specific antibodies according to standard methods. Anti-phospho-ERK1 and anti-phospho-ERK2 antibodies were obtained from Cell Signaling Technology (Beverly, Mass.). Anti-phospho-CREB antibody was obtained from Upstate Biotechnology (Lake Placid, N.Y.). Anti-phospho-DARPP32 antibodies were used that had been produced according to the methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, (each of which is incorporated herein by reference in its entirety). These methods were used to produce phosphorylation state-specific antibodies having specificity for Thr34-phosphorylated and Thr75-phosphorylated DARPP-32.

5.2. Results

The experimental results are shown in Table 1.

TABLE 1

| Time (min) | Eticlopride (0.5 mg/kg, i.p.) ± SEM | Haloperidol (0.2 mg/kg, i.p.) ± SEM | Clozapine (5 mg/kg, i.p.) ± SEM |
|---|---|---|---|
| Thr34-DARPP-32 | | | |
| 0 | 100 11 | 100 11 | 100 8 |
| 15 | 192 23** | 195 25** | 188 19* |
| 30 | 226 26** | 196 23** | 209 27** |
| 60 | 190 18** | 155 34 | 222 47** |
| Thr75-DARPP-32 | | | |
| 0 | 100 8 | 100 5 | 100 6 |
| 15 | 80 10 | 133 18 | 179 20** |
| 30 | 70 8* | 144 23 | 216 19** |
| 60 | 80 6 | 138 31 | 203 26** |
| Thr202- and Tyr204- ERK1 | | | |
| 0 | 100 6 | 100 6 | 100 7 |
| 15 | 223 20** | 231 19** | 90 11 |
| 30 | 207 16** | 187 14** | 75 12 |
| 60 | 170 20** | 169 19** | 33 6** |
| Thr185- and Tyr187- ERK2 | | | |
| 0 | 100 3 | 100 7 | 100 7 |
| 15 | 132 10* | 151 15** | 62 8** |
| 30 | 97 13 | 114 13 | 41 6** |
| 60 | 96 10 | 107 14 | 15 2** |
| Ser133-CREB | | | |
| 0 | 100 9 | 100 8 | 100 6 |
| 15 | 167 16** | 148 19* | 51 4** |
| 30 | 146 15* | 131 23 | 62 6** |
| 60 | 123 12 | 114 12 | 57 4** |

Data represent mean ± S.E.M.
*P, <0.05,
**P < 0.01 versus control (time "0"); one-way ANOVA followed by Dunnett's test.

The results showed that treatment of animals in vivo with the various anti-psychotic drugs produced distinct phosphorylation patterns of the intracellular signaling proteins studied. Both haloperidol (0.2 mg/kg) (a typical anti-psychotic) and eticlopride (0.5 mg/kg) (a selective dopamine D2 receptor antagonist) produced significant increases in the levels of phospho-ERK1 and phospho-ERK2, as well as phospho-CREB. The protein phosphorylation was maximally increased 15 minutes following drug administration. Phospho-ERK2 levels returned to control levels 30 minutes after haloperidol or eticlopride administration. Phospho-CREB levels returned to control levels 30 minutes after haloperidol administration or 60 minutes after eticlopride administration. Phospho-ERK1 levels were still significantly higher than control values at 60 minutes.

In contrast, treatment with clozapine (5.0 mg/kg) (an atypical anti-psychotic) produced a rapid decrease in the levels of phospho-ERK2 and phospho-CREB at 15, 30 and 60 minutes. In addition, levels of phospho-ERK1 were decreased at 60 minutes after administration of the atypical anti-psychotic.

In the case of DARPP-32 phosphorylation, all three drugs increased phosphorylation at Thr34 site of DARPP-32. With administration of a typical anti-psychotic such as haloperidol, Thr34 phosphorylation increased for up to 30 minutes, but at 60 minutes, there was no statistical difference from controls. In the case of phosphorylation at the Thr-75 site of DARPP-32, only clozapine treatment significantly increased phosphorylation levels at 15, 30 and 60 minutes. Eticlopride decreased DARPP-32 phosphorylation at Thr75 of DARPP-32 at 30 minutes, while haloperidol was without effect.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for identifying an agent to be tested as an atypical anti-psychotic treatment for a psychotic disorder, comprising:
    contacting striatal cells or tissue with the agent to be tested,
    detecting the phosphorylation levels of DARPP-32 at Thr75, ERK1 at Thr202 and Tyr204, ERK2 at Thr185 and Tyr187 and CREB at Ser133 in the striatal cells or tissue contacted with the agent;
    detecting the phosphorylation levels of DARPP-32 at Thr75, ERK1 at Thr202 and Tyr204, ERK2 at Thr185 and Tyr187 and CREB at Ser133 in the striatal cells or tissue not contacted with an agent;
    determining whether a predetermined criteria has been met, wherein the criteria comprises a phosphorylation level of Thr75 in DARPP-32 in the treated cells or tissue greater than the untreated cells or tissue, and phosphorylation levels of Thr202 and Tyr204 in ERK1, Thr185 and Tyr187 in ERK2 and Ser133 in CREB in the treated cells or tissue less than the untreated cells or tissue; and
    wherein the agent is identified for testing as an atypical anti-psychotic treatment if the agent meets the criteria.

2. The method of claim 1 wherein the psychotic disorder is schizophrenia.

3. The method of claim 1 wherein the at least one of the subjects is a schizophrenic animal model.

4. The method of claim 1 wherein the detecting step is performed at least 15 minutes and no longer than 30 minutes after the striatal cells or tissue has been contacted with the agent.

5. The method of claim 1 wherein the detecting step is performed at least 30 minutes and no longer than 60 minutes after the striatal cells or tissue has been contacted with the agent.

6. The method of claim 1 wherein the phosphorylation level of Thr75 in DARPP-32, Thr202 and Tyr204 in ERK1, Thr185 and Tyr187 in ERK2 or Ser133 in CREB is detected with a phosphospecific antibody.

7. The method of claim 1 wherein the phosphorylation level of Thr75 in DARPP-32, Thr202 and Tyr204 in ERK1, Thr185 and Tyr187 in ERK2 or Ser133 in CREB is detected by measuring a kinase activity.

8. The method of claim 1 wherein the phosphorylation level of Thr75 in DARPP-32, Thr202 and Tyr204 in ERK1, Thr185 and Tyr187 in ERK2 or Ser133 in CREB is detected by measuring a phosphatase activity.

9. The method of claim 1 wherein the striatal cells or tissue is in a whole animal when contacted by the agent.

10. The method of claim 1 wherein DARPP-32 is human DARPP-32.

11. The method of claim 1 wherein CREB is human CREB.

12. The method of claim 1 wherein ERK1 is human ERK1.

13. The method of claim 1 wherein ERK2 is human ERK2.

14. The method of claim 1 wherein DARPP-32 is mouse DARPP-32.

15. The method of claim 1 wherein CREB is mouse CREB.

16. The method of claim 1 wherein ERK1 is mouse ERK1.

17. The method of claim 1 wherein ERK2 is mouse ERK2.

* * * * *